US010247731B2

(12) United States Patent
Parenteau et al.

(10) Patent No.: US 10,247,731 B2
(45) Date of Patent: Apr. 2, 2019

(54) SYSTEM FOR IMMUNOTHERAPY TARGETING TUMOR PROPAGATION AND PROGRESSION

(71) Applicant: Ingenium Biotherapy Corporation, Benson, VT (US)

(72) Inventors: Nancy L. Parenteau, Fair Haven, VT (US); Joseph C. Laning, Southborough, MA (US); Janet H. Young, Boerne, TX (US)

(73) Assignee: Verik Bio, Inc., Benson, VT (US)

( * ) Notice: Subject to any disclaimer, the term of this patent is extended or adjusted under 35 U.S.C. 154(b) by 1269 days.

(21) Appl. No.: 13/774,644

(22) Filed: Feb. 22, 2013

(65) Prior Publication Data

US 2013/0273083 A1   Oct. 17, 2013

Related U.S. Application Data

(60) Provisional application No. 61/601,893, filed on Feb. 22, 2012.

(51) Int. Cl.
| | |
|---|---|
| *C12N 5/00* | (2006.01) |
| *C12N 5/02* | (2006.01) |
| *G01N 33/574* | (2006.01) |
| *C12N 5/0783* | (2010.01) |
| *C12N 5/09* | (2010.01) |
| *C12N 5/095* | (2010.01) |
| *G01N 33/50* | (2006.01) |
| *C07K 14/705* | (2006.01) |
| *C07K 14/74* | (2006.01) |
| *A61K 38/17* | (2006.01) |
| *A61K 35/17* | (2015.01) |

(52) U.S. Cl.
CPC ......... *G01N 33/574* (2013.01); *A61K 35/17* (2013.01); *A61K 38/1774* (2013.01); *C07K 14/70503* (2013.01); *C07K 14/70539* (2013.01); *C12N 5/0638* (2013.01); *C12N 5/0693* (2013.01); *C12N 5/0695* (2013.01); *G01N 33/50* (2013.01); *C12N 2500/05* (2013.01); *C12N 2501/01* (2013.01); *C12N 2501/2301* (2013.01); *C12N 2501/24* (2013.01); *C12N 2501/25* (2013.01); *C12N 2501/48* (2013.01); *C12N 2501/90* (2013.01)

(58) Field of Classification Search
None
See application file for complete search history.

(56) References Cited

U.S. PATENT DOCUMENTS 7,713,710 B2 *   5/2010  Clarke et al. .................. 435/7.1
7,781,179 B2 *   8/2010  Weissman et al. ............. 435/7.1
8,309,354 B2    11/2012  Mather
8,569,055 B2 *  10/2013  Gutova et al. ................. 435/366
2008/0175870 A1  7/2008  Mather

OTHER PUBLICATIONS

Maenhaut et al ( Carcinogenesis, 20010, v.31 pp. 149-158.*
Ceder, et al., "The characterization of epithelial and stromal subsets of candidate stem/progenitor cells in the human adult prostate", Eur. Urol., 53:524-32 (2007).
Collins, et al., "Prospective identification of tumorigenic prostate cancer stem cells", Cancer Res, 65(23):10946-51 (2005).
Disis, et al., "Use of tumour-responsive T cells as cancer treatment", Lancet, 373 (9664):673-83 (2009).
Park, et al., "Treating cancer with genetically engineered T cells", Trends Biotechnol., 29(11):550-7 (2011).
Pellegatta, et al., "Neurospheres enriched in cancer stem-like cells are highly effective in eliciting a dendritic cell-mediated immune response against malignant gliomas", Cancer Res., 66(21):10247-52 (2006).
Rosenberg, et al., "Adoptive cell transfer: a clinical path to effective cancer immunotherapy", Nat Rev Cancer, 8(4):299-308 (2008).
Singh, et al., "Identification of a cancer stem cell in human brain tumors", Cancer Res., 63(18):5821-8 (2003).
Subklewe, et al., "Dendritic cells expand Epstein Barr virus specific CD8+ T cell responses more efficiently than EBV transformed B cells", Hum. Immunol., 66(9):938-49 (2005).
International Search Report for corresponding PCT application PCT/US2013/027445, dated Jun. 5, 2013.
Gillet, et al., "Redefining the relevance of established cancer cell lines to the study of mechanisms of clinical anti-cancer drug resistance", PNAS, 108:18708-9 (2011).
Jaggupilli and Elkord, "Significance of CD44 and CD24 as cancer stem cell markers: an enduring ambiguity", Clin Dev Immunol., 708036 (2012).
Jones, et al., "Lentiviral vector design for optimal T cell receptor gene expression in the transduction of peripheral blood lymphocytes and tumor-infiltrating lymphocytes", Hum Gene Thor., 20(6):630-40 (2009).
Langdon, et al., "Characterization and properties of nine human ovarian adenocarcinoma cell lines",Cancer Res, 48:6166-72 (1988).
Oulette, et al., "Characterization of three new serous epithelial ovarian cancer cell lines", BMC Cancer, 8:152—(2008).
Pan, et al., "Establishment of human ovarian serous carcinomas cell lines in serum free media", Methods, 56:432-9 (2012).
Roberts, "Isolation and establishment of human tumor stem cells", Methods Cell Biol., 86:325-42 (2008).

(Continued)

*Primary Examiner* — Michail A Belyavskyi
(74) *Attorney, Agent, or Firm* — Pabst Patent Group LLP

(57) ABSTRACT

Finding biologically relevant cancer markers is key to developing an effective treatment. Once specific antigens have been identified that are present on the cell population responsible for propagating tumors, T cells can be genetically altered to target these antigens and then used for personalized T cell therapy. A method to identify and select peptide antigens that effectively associate with and are presented by host HLA surface molecules originating from tumor cells responsible for the persistence and propagation of a cancer has been developed. The system of using these data to produce T cells engineered to express T cell receptors recognizing the peptide antigens is used in the production of a personalized adoptive T cell therapy for cancer that eliminates the cells capable of tumor propagation and cancer progression. The system is especially useful in the production of cancer treatments to achieve complete durable remission of cancers of epithelial origin.

1 Claim, 9 Drawing Sheets

(56) References Cited

OTHER PUBLICATIONS

Sethi, et al., "A highly tilted binding mode by a self-reactive T cell receptor results in altered engagement of peptide and MHC", J Exp Med. 208(1):91-102 (2011).
Strauss, et al., "Analysis of epithelial and mesenchymal markers in ovarian cancer reveals phenotypic heterogeneity and plasticity", PLOSOne, 6:e16186 (2011).
Takahashi and Yamanaka, "Induction of pluripotent stem cells from mouse embryonic and adult fibroblast cultures by defined factors", Cell. 126(4):663-76 (2006).
Tomuleasa, et al., "Isolation and characterization of hepatic cancer cells with stem-like properties from hepatocellular carcinoma", J Gastrointestin Liver Dis., 19(1):61-7 (2010).

\* cited by examiner

1. Tissue explants undergo regenerative activation. The RC cells selectively proliferate and are captured.

| Normal Control | Cancer |
|---|---|
| N.1 Normal Epithelial Tissue Sample | C.1 Tumor Tissue Sample |
| N.2.a Proliferating N-RC Cells (primary) | C.2.a Proliferating C-RC Cells (primary) |
| N.2.b Proliferating N-RC Cells (passaged) | C.2.b Proliferating C-RC Cells (passaged) |

2. Regeneration-capable cells are subjected to one or more differentiating conditions in vivo and in vitro.

| | |
|---|---|
| N.3 N-RC (control) under EMT-promoting conditions | C.3 C-RC under EMT-promoting conditions |
| N.4 N-RC under differentiating conditions | C.4 C-RC under differentiating conditions |
| N.5 N-RC in vivo grafts (kidney capsule) | N.5 C-RC in vivo grafts (kidney capsule) |

3. Proteins from the cell and tissue samples are digested into peptides and analyzed using Multidimensional Protein Identification Technology (MUDPIT) LC-MS/MS to generate a representative proteome of each sample type.

4. Tissue and specialized RC proteomes are analyzed against each other to validate and prioritize C-RC-relevant proteins.

FIG. 2B

Modified from Figure 3.
Jones, S., et al. Hum. Gene Ther., 2009

Modified from Figure 3.
Jones, S., et al. Hum. Gene Ther., 2009

SYSTEM FOR IMMUNOTHERAPY TARGETING TUMOR PROPAGATION AND PROGRESSION

RELATED APPLICATIONS

This application claims priority to U.S. Ser. No. 61/601,893 filed Feb. 22, 2012, the teachings of which are incorporated herein.

FIELD OF THE INVENTION

The invention is generally directed to methods and compositions for personalized T cell therapy that eliminates or substantially reduces the number of cells capable of tumor propagation and cancer progression.

BACKGROUND OF THE INVENTION

Tumors are variable and heterogeneous and therefore could escape immunotherapy targeted to a specific antigen. For an effective cancer treatment, it is important to target the cell population responsible for propagating a tumor and causing tumor progression.

Adoptive cell therapy (ACT) is the transfer of immune cells as a means of enhancing immune functionality. Cytolytic T lymphocytes (CTL) expanded from a patient's tumor infiltrating lymphocytes (TIL) are capable of enhancing the killing of tumor cells to cause regression of the tumor and in some patients, a durable remission effectively curing the patient (Rosenberg, *J. Nat. Cancer Inst.* 86(15):1159-66 (1994)). However, the use of autologous TIL as a personalized cancer therapy has several drawbacks: 1) adequate numbers of TILs can only be generated in about 40-50% of patients (P. Hwu, *Presentation, Society for Immunotherapy of Cancer,* 25$^{th}$ *Annual Meeting,* Oct. 1, 2010), 2) it takes 4-6 weeks to generate enough T cells and 3) the antigens targeted by the TIL are diverse (Nishimura, et al. *J. Immunotherapy with Emphasis on Tumor Immunology: Official Journal of the Society for Biological Therapy* 16(2):85-94 (1994); Rosenberg, 1994; Shilyansky, *Proc. Nat, Acad. Sci. USA* 91(7): 2829-33 (1994)), which makes its effectiveness difficult to standardize (Schwartzentruber D J, et al. *J Clin Oncol.* 12(7):1475-83 (1994)) and ensure that the TIL target clinically meaningful antigens.

One way to control the targeted T cell killing more selectively without requiring expansion of patient TIL is to genetically engineer T cell receptors (TCR) to be specific for single known antigens. ACT using CTL has shown exceptional promise in the treatment of certain non-epithelial and viral-induced cancers. However the paucity of validated antigens has limited the use of engineered T cells to a small number of well-characterized antigens (e.g., gp100, NY ESO-1, WT-1, MART-1, MAGE-3), although they too lack definitive data as to how they relate to the tumor propagating population of the cancers (for example, the cancer testis antigen NY ESO-1 is a potentially important ACT target in epithelial ovarian cancer yet differences in intratumor and intertumor expression of the antigen vary (Woloszynska-Read et al., *Clin. Canc. Res,* 14:3283 (2008)) and must be better understood for effective cancer immunotherapy using this antigen).

To achieve ACT with curative potential, a way is needed to validate the relationship of presently known and novel antigens to tumor propagation and progression as well as to determine antigen cross-reactivity with normal cells, particularly those undergoing normal wound repair and regeneration. This information would enable the safe and effective targeting of ACT using engineered T cells and expand the clinical application of ACT, particularly to cancers originating from vital organs where the use of tissue-specific markers (e.g. MART-1 against melanocytes) is not an option.

Such a solution is particularly needed to effectively treat cancers arising from endogenous functional mutations (as opposed to viral mutations), which have proven to be particularly challenging. Some believe that 'shared unique' tumor antigens would make the ideal target for adoptive engineered T cell therapy and that antigens arising from specific mutations will only identify a small subset of tumors within a certain cancer type and stage (Paschen, *T Cell Antigens in Cancer, Chapter* 1, Tumor-Associated Antigens, Gires and Seliger eds. Wiley-VCH GmBH & co. KGaA, Weinheim, (2009)). Researchers have postulated that fully cataloging genetic rearrangements and transcriptional changes is a way to overcome this limitation: "Central to expectations of accelerated target discovery is the perception that genome, transcriptome and proteome analyses will lead to the discovery of molecules against which cancer therapeutics might be targeted" (Strausberg et al., *Nature* 429 (6990):469-474 (2004)). Yet oncogenomics is of limited use for curative targeting of engineered T cell therapy because it merely associates the presence of a genetic alteration with the stage of the tumor. While this information can be of prognostic value it does not provide the information necessary to determine the mutation's appropriateness for curative targeting. It is widely appreciated that without being able to link genetic changes to functional biology, genomic targets will not translate to drugs or biomarkers that can be used for highly effective biologic therapeutics such as ACT. An additional practical consideration that confounds 'omics' attempts at determining the relevance of biomarkers directly from tissue samples is the significant bias that is introduced with even small changes in tumor sample handling and processing (Ransohoff and Gourlay, *J Clin Oncol* 28(4):698-704 (2010).

Researchers have also employed biological methods as a way to better understand cancer and identify therapeutic targets. They have recognized that accurate determination of the predictive and therapeutic significance of cancer markers depends on the comparison of expression signatures in normal lineages with those of different tumor subtypes (Visvader, et al. *Nature* 469(7330):314-322 (2011)). But population heterogeneity and a growing realization that the tumor cell population is both variable and dynamic (Gupta, et al. *Nature medicine* 15(9):1010-1012 (2009); Gupta, et al. *Cell* 146(4):633-644 (2011)), has made meaningful comparison difficult.

Despite the heterogeneous nature of a tumor, its histopathology and gene expression can appear relatively stable as it progresses from localized disease to metastatic and end-stage disease (Visvader, et al. *Nature* 469(7330):314-322 (2011)). Also, tumor phenotype does not necessarily translate to tumor histopathology or lineage marker expression (Visvader, et al. *Nature* 469(7330):314-322 (2011)). Leukemia and solid tumors can maintain a differentiation hierarchy (Shipitsin, et al. *Lab Invest.* 88(5):459-63 (2008)), but the relationship within the hierarchy is disrupted, where cancer-propagating cells are similar to progenitor and stem cells in some ways, but different in other ways. Because of this, cancer has been referred to as a "disease of differentiation." More precisely, cancer is a disease of genes operating in the context of differentiation. Therefore what is needed is a way to simplify cancer's dynamic nature and variability within a context of functional differentiation so that therapeutic targets with curative potential can be identified.

Analysis of fractionated cells, single cells and in situ expression of biomarkers in a static condition are current approaches to identifying tumor subpopulations. However they do not provide a means to establish the relevance of the biomarker to the tumor propagating subpopulation(s), which is needed to ensure curative therapeutic targeting.

Although many have attempted to identify and, select out cells at varying stages of differentiation using known markers, these cell compartments cannot be mechanically selected with either stem cell or differentiation markers and then expanded for analysis because 1) regeneration-capable cells are identified primarily by their behavior and 2) it is not certain to what extent regeneration-capable tumor propagating cells will express stem cell or differentiation markers (Tysnes, *Neoplasia* 12(7):506-515 (2010)). The regeneration-capable cells of a cancer (Maenhaut, *Carcinogenesis* 31(2):149-158 (2010)), are referred to herein as the "C-RC", and encompass all regeneration capable cells regardless of their cell compartment of origin, and may encompass cancer cells with properties of normal stem cells, but need not be limited to or related to a native stem cell compartment. Therefore what is needed is the opposite approach, i.e., a way to first identify and isolate the cell subpopulation based on its function, and then determine its identifying markers.

Researchers have looked to fetal cells as a way to identify stem and progenitor cell markers because fetal cells, in the process of organogenesis, will have a naturally rich generative cell pool (U.S. Pat. No. 7,078,231 to Roberts, et al.). While many cancers may arise in progenitor cells, abnormalities can occur in the stem, progenitor, or transit amplifying cell compartments (Tysnes, *Neoplasia* 12(7):506-15 (2010)). This makes the tactic of relying on the natural generative pool present in fetal tissue (U.S. Pat. No. 7,078,231 to Roberts, et al.) or derived from adult tissue through regenerative activation (U.S. patent publication US2006/0121605 by Parenteau, et al.) inadequate for cancer antigen identification for curative engineered T cell therapy, because it requires one to make assumptions regarding the applicability of the findings to a tumor's ability to grow and progress. Not all tumor types and stages within a particular cancer indication will have the same relationship between these compartments, yet this relationship will be important to tumor heterogeneity and progression.

The relationship between cell compartments within a tumor cell population cannot be appreciated by histopathology, genomics, proteomics or static marker analysis, if the analysis ultimately lacks the ability to link them to cell compartment interaction and behavior. Current methods have fallen short in their ability to distinguish between causative and contributing cell populations within a cancer type and stage. Evidence of this difficulty is the long running debate as to the clinical significance of cancer stem cells identified by these means.

Newer in vitro culture methods have been used to better understand the tumor cell population and its potential, but these methods are still inadequate to derive the key functional subpopulation responsible for tumor propagation and progression. For example, Gillet et al., *PNAS*, 108:18708 (2011)) determined that sixty established cancer cell lines (NCI60 panel) bear greater genomic resemblance to each other both in vivo and in vitro, regardless of tissue origin, than to primary tumors, indicating a need for a better way to maintain the fidelity of gene expression, epigenetic influences, cell relationships and cell response. This fidelity is particularly needed to discriminate robust yet safe peptide targets for CTL therapy. Using ovarian cancer as an example, in deriving of a tumor cell lines from ovarian cancers, Strauss et al. (Strauss et al. *PLOSOne*, 6:e16186 (2011)) found that ovarian cancer rapidly lost its epithelial component in culture, leaving a dominant yet seemingly hybrid epithelial/mesenchymal phenotype with an unclear relationship to the native tumor cells.

Although spheroid culture methods have been shown to maintain what are considered to be stem and progenitor cells (more likely primarily transit amplifying cells) within a heterogeneous population that can be expanded on a limited basis, the ability to dissect the cell populations from spheroids is difficult, requiring disaggregation of the spheres and clonal assays (Al-Hajj, et al. *Proc. Nat. Acad. Sci. USA* 100(7):3983-3988 (2003)), which then destroys the biological context. Also, evidence of selective regenerative stimulation of the progenitor pool is lacking in these methods when used to culture normal stem and progenitor cells (Parenteau, *Cell Differentiation, In Vitro Mammalian.* Encyclopedia of Industrial Biotechnology: Bioprocess, Bioseparation, and Cell Technology, John Wiley & Sons: 1-15 (2009)) and will not selectively stimulate the tumor's C-RC subpopulation, which is needed for functional identification. For example, derivation of a "cancerous" progenitor-like population in spheroid culture has required immortalizing normal ovarian epithelial cells with hTERT and causing partial transformation by overexpressing the oncogenes CMYC, KRAS or BRAF (Lawrenson, et al. *Carcinogenesis* 32(10):1540-1549 (2011)).

The gene signature from three-dimensional culture has been shown to provide prognostic value in breast cancers by comparing their genomic signatures (Martin, et al., *PLoS ONE* 3(8):e2994 (2008)). However like spheroid culture, it is incapable of functionally identifying and isolating the tumor C-RC subpopulation within the heterogeneous, differentiating tissue. Although 3-D culture serves as an valuable comparator, it favors differentiation and resulting heterogeneity, and does not selectively stimulate the regenerative tumor population. Therefore 3-D culture can be a valuable tool in assessing how a tumor develops and differentiates from the C-RC population but it does not isolate the C-RC population.

Animal models have served as an alternative way to analyze tumor biology in a more complex context. However animal implantation, while a functional test of the population, is often not a reliable estimate of tumor propagating cells (Maenhaut, et al. *Carcinogenesis* 31(2):149-58 (2010)). On one hand, the immune-compromised mouse can have some residual immunity, which can limit implantation and lower the tumor's ability to recruit cells of innate immunity that provide the stimulatory factors important for tumor development, in particular stromal and vascular recruitment (Shipitsin, et al., *Lab. Invest.* 88(5):459-463 (2008)). On the other hand, experience with tumorigenic cancer cell lines indicates that the development of tumors in mice from cultured cancer cells is a growth property that can be acquired over time, and need not relate to regeneration of the native tumor. Therefore tumor formation in animals in itself is insufficient to identify the implanted cells as the C-RC population of the native tumor i.e., the ability to form tumors in mice confirms a C-RC population of a tumor only if the cells used for implantation have been functionally identified as C-RC, prior to implantation. Using animal models as a tool to show recapitulation of the original tumor histology is important in demonstrating that the cells isolated are C-RC.

U.S. Pat. No. 8,309,354 discloses a method of deriving a population of cells containing cancer stem cells, by dissociating solid human tumors and culturing dissociated cells and small cell aggregates in serum-free conditions to obtain cancer stem cell lines that do not senesce upon serial passage, express certain stem cell markers that can vary between cancer types, and exhibit a high efficiency of tumor formation in mice. However the serum-free conditions used to generate these lines allow for the growth and persistence of a stromal cell component, which eventually gives way to a cancer stem cell-like epithelial cell population after an extended period (months) in culture. Similarly, Pan, et al. (Pan, et al. *Methods* 56:432 (2012)) describes deriving ovarian cancer stem cell-like lines where epithelial cells and stromal cells propagate in primary culture. A substantially pure population of epithelial cells can take 3-6 months, assuredly leading to substantial changes in the cancer cell population.

Recent advances in murine immune-compromised animal model development have given rise to several highly versatile strains expressing a variety of human immune markers in compartmentally valid patterns. These technologically advanced animals allow Human Leukocyte Antigen (HLA) matched and tissue specific expansion of selected tumor C-RC populations in vivo under conditions that enable their examination from both oncologic and immunologic perspectives (Covassin, *Clin Exp Immunol* 166(2):269-280 (2011)). In addition, this versatile mouse strain can be used as an in vivo incubator, as demonstrated by Bankert, et al. *PLoS ONE* 6(9):e24420 (2011) who showed that serous ovarian tumors could be successfiffly implanted and expanded in the NOD-scid IL2R$\gamma^{null}$(NSG) strain. However tumor heterogeneity is maintained and the tumors remain complex. Rather like 3-D organotypic models, use of these animals can serve as an important component in testing the robustness of expression and prioritization of C-RC-relevant tumor markers as well as potential C-RC behavior like epithelial-mesenchymal transition (EMT) and the associated potential for metastasis, once a C-RC population as well as ways to identify the population are in hand. In addition, these animals can be used for primary tumor expansion before in vitro derivation of the C-RC population with the added benefit for ACT in that TIL resident to the implanted tumor have been shown to be expanded as well. The ability to expand nascent TIL within these animal models provides the added opportunity to obtain valuable sources of tumor-specific T cells via standard antibody-based magnetic selection methods for TCR selection.

A method or technology for the derivation of a C-RC population of high fidelity and translational value for applications such as the targeting cancer cells for immune killing should be 1) inclusive, as C-RC-enabling mutation can arise from any dividing cell compartment within an epithelial lineage and identification based on human stem cell markers will be ambiguous and varied 2) response-based, for identification and selection, as only then can one be assured marker expression relates to the clinically relevant cell population and 3) high fidelity where technology does not artificially contribute to a shift in cell response or phenotype but permits a rapid, self-directed response through autocrine and paracrine signaling. Then, a method or technology useful for targeting a curative adoptive T cell therapy must be 1) capable of safely discriminating the C-RC population, i.e., those cells capable of continued tumor propagation and progression, and 2) able to link the expression of tumor markers to the C-RC population in vivo.

Despite many genomic, proteomic and biological attempts, ways to solve the conundrum of linking marker expression to the function of cells compartment within the tumor have not been obvious to researchers working to determine the biological significance of cancer markers. Despite genomics and proteomics yielding a large number of potential cancer markers (Polanski, et al. *Biomarker insights* 1:1-48 (2007)) and efforts to prioritize their therapeutic relevance (Cheever, et al. *Clin Cancer Res.* 15(17):5323-37 (2009)), researchers have had difficulty demonstrating their relevance as therapeutic targets. Researchers in the field recognize that this is due to the complexity of the tumor population and a lack of adequate systems to link the biology of a complex epithelial tumor to clinically applicable marker expression (Tysnes B B, *Neoplasia* 12(7):506-15 (2010)). Evidence of this deficiency is the continued debate as to the therapeutic relevance of cancer stem cells and in particular, the difficulty researchers have had in attempting to grapple with how to handle observed differences (Gupta, et al., *Nat. Med.* 15(9):1010-12 (2009); Maenhaut, et al. *Carcinogenesis* 31(2):149-58 (2010); Shipitsin, et al., *Lab. Invest.* 88(5):459-63 (2008); Pantic, *J. Biosci.* 36(5):957-61 (2011)) and ambiguous identifying markers (Jaggupilli and Elkord, *Clinical and Developmental Immunology* (2012), Article ID 708036).

It is clear that a functional way of deciphering cell capabilities within and between the cell compartments of a tumor sample is needed for practical and effective immunological targeting.

It is therefore an object of the present invention to provide a way of deciphering cell capabilities within and between the cell compartments of a tumor sample.

It is a further object of the present invention to focus a cancer's dynamic nature and variability by engendering a functional reponse to regenerative pressure in vitro so that key therapeutic targets can be identified.

It is a further object of the present invention to isolate the clinically relevant tumor cell population.

It is a further object of the present invention to use the clinically relevant population of a cancer type and stage as an antigen source to identify markers suitable for curative ACT using engineered T cells against that cancer type and stage.

It is a still further object of the present invention to use engineered T cells against markers that identify the clinically relevant tumor subpopulation to purposely design curative therapies.

It is another object of this invention to identify and validate the therapeutic significance of a putative cancer marker without the need for genomic screening, which can be prone to high levels of artifact and both positive and negative spurious findings.

It is a further object of the present invention to provide a means for deriving functional populations from a tumor and for using them to recapitulate tumor development in vitro and in vivo where bias and artifact can be identified, controlled and eliminated.

It is another object of the present invention to eliminate the need to presume the expression or clinical significance of a putative marker, such as a stem cell marker, in order to either identify or isolate the most clinically important tumor cell population.

It is another object of the present invention to provide methods and systems for programming T cells to selectively attack important tumor cells involved in proliferation, or invasion in an individual.

It is another object of the present invention to significantly reduce the risk and cost of development by functionally validating and prioritizing ACT targets prior to costly process development and clinical testing.

SUMMARY OF THE INVENTION

Finding biologically relevant cancer markers is key to developing an effective treatment. Once specific antigens have been identified that are expressed by the cell population responsible for propagating tumors, T cells can be genetically altered to target these antigens and then be used for personalized T cell therapy. A method to identify and select peptide antigens that are presented by host HLA surface molecules originating from tumor cells responsible for the persistence and propagation of a cancer has been developed. The system of using these data to produce T cells engineered to express T cell receptors recognizing the peptide antigens is used in the production of a personalized adoptive T cell therapy for cancer that eliminates the cells capable of tumor propagation and cancer progression. The system is especially useful in the production of cancer treatments to achieve complete durable remission of cancers of epithelial origin.

The system is distinguished from other methods by at least the addition of a regenerative challenge that, in normal tissue, will foster progenitor activation within adult epithelia in vitro and subsequently a substantial increase in a progenitor pool of small epithelial cells between 9-14 microns in diameter. Prior methods of sorting the rare stem/progenitor cells from mature organs has led to identification of markers, but removing and culturing them requires complex growth factor mixtures, or specialized culture such as spheroid culture, which do not result in progenitor pool expansion. This has limited cancer stem cell research (where the true C-RC subpopulation(s) will either be based in the progenitor compartment or be progenitor-like), and led to two persistent deficiencies: 1) the inability to analyze the normal progenitor cell population from mature tissues—an important comparator for safe translation; and 2) the inability to functionally dissect out the C-RC of a tumor, which could contain progenitor cells, or progenitor-like cells consisting of abnormal transit amplifying cells. The method described herein identifies the C-RC population and collects it via selective regenerative pressure. This is then used to design a selective personal treatment for a specific type and stage of cancer.

DETAILED DESCRIPTION OF THE INVENTION

Figure 1:
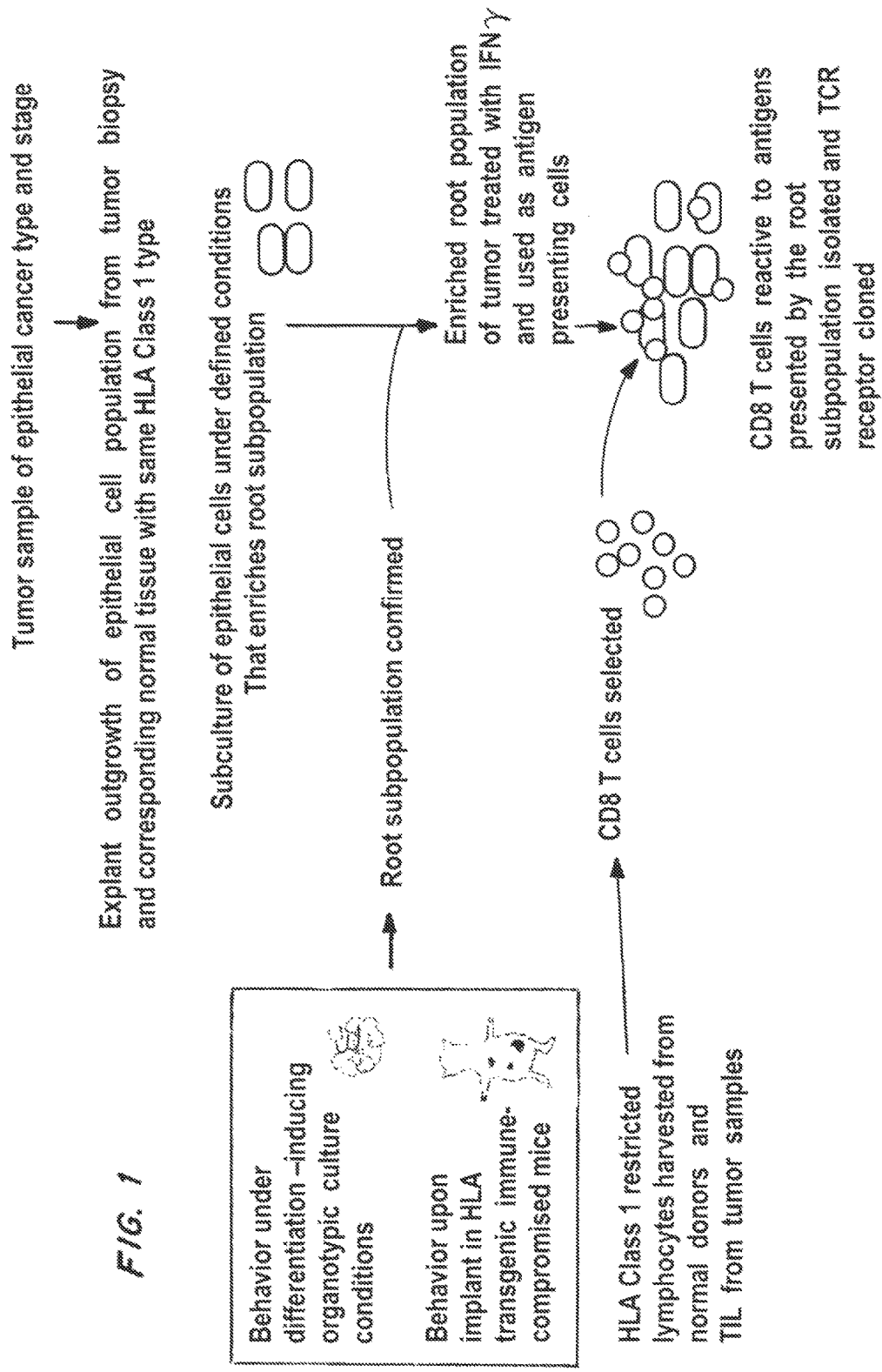
FIG. 1 is a flow chart depicting a process for identifying and prioritizing antigens and producing a T cell receptor (TCR) panel.
Figure 1:
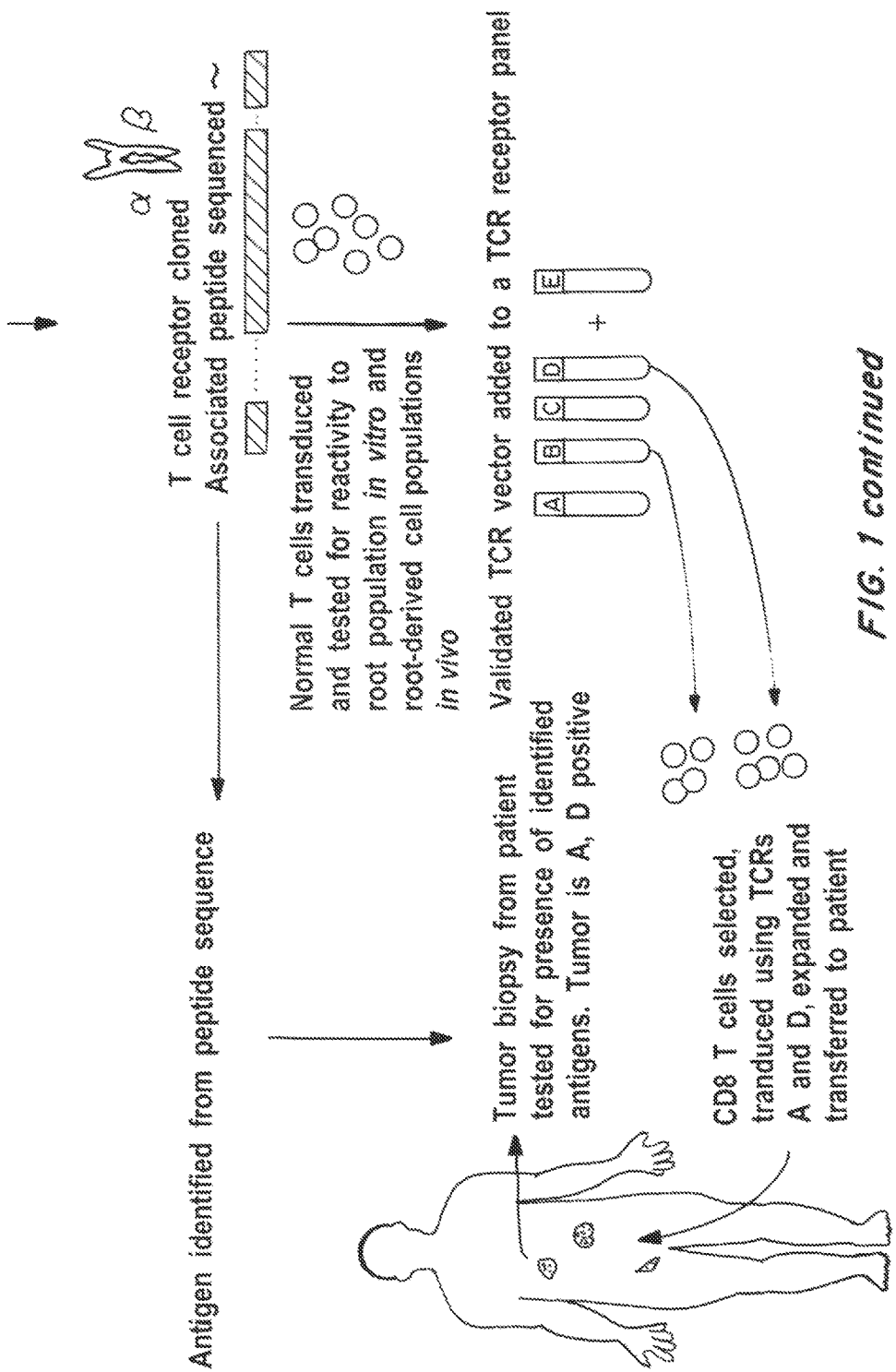

The significance of regenerative activation in cancer research has not been apparent, in part because the techniques developed for embryonic stem cell research (naturally high in stem cells and progenitor offspring) will not activate expansion of a progenitor pool in mature tissues. This has led to a commonly held assumption that the progenitor population in mature normal tissues is virtually indistinct from a more limited transit amplifying population even though evidence from embryonic organogenesis points to the existence and distinct control of a progenitor pool in the organ rudiment (Parenteau N L, et al., *Curr Top Dev Biol.* 64:101-39 (2004)).

In contrast, methods for the production of adoptive T cell therapy have advanced to the point of clinical utility (Rosenberg S A, *Proc. Nat. Acad, Sci. USA* 105(35):12643-44 (2008)). Yet until now, adoptive T cell therapy has suffered serious practical limitations preventing its widespread applicability, availability and use (Restifo N P, et al. *The Scientist.* (Apr. 11, 2011)).

The disclosed methods enable the translation of ACT against cancers of epithelial origin, especially epithelial cancers of vital organs like the pancreas, liver, lung and gut among others. The disclosed method for producing a personalized adoptive T cell therapy for cancer eliminates the cells capable of tumor propagation and cancer progression (collectively, the "C-RC" population of a cancer). The method can be used to engineer T cell therapies against previously unknown C-RC-relevant cancer markers or known cancer markers.

I. Definitions

The terms "adoptive cell therapy" and "adoptive cell transfer" refer to the transfer of T cells reactive to a patient's cancer back into the patient. The T cells are preferably obtained from the patient and genetically engineered using the disclosed methods to be reactive against the cancer.

The term "individual," "host," "subject," and "patient" are used interchangeably to refer to any individual who is the target of administration or treatment. The subject can be a vertebrate, for example, a mammal. Thus, the subject can be a human or veterinary patient.

The term "therapeutically effective" refers to the amount of the composition, e.g., engineered T cells, which is of sufficient quantity to ameliorate one or more causes or symptoms of a disease or disorder, e.g., cancer growth or metastasis. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "treatment" refers to the medical management of a patient with the intent to cure, ameliorate, stabilize, or prevent one or more symptoms of a disease, pathological condition, or disorder. This term includes active treatment directed specifically toward the improvement of a disease, pathological condition, or disorder, and causal treatment that is treatment directed toward removal of the cause of the associated disease, pathological condition, or disorder. In addition, this term includes palliative treatment, that is, treatment designed for the relief of one or more symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "neoplastic cell" refers to a cell undergoing abnormal cell proliferation ("neoplasia"). The growth of neoplastic cells exceeds and is not coordinated with that of the normal tissues around it. The growth typically persists in the same excessive manner even after cessation of the stimuli, and typically causes formation of a tumor.

The term "tumor" or "neoplasm" refers to an abnormal mass of tissue containing neoplastic cells. Neoplasms and tumors may be benign, premalignant, or malignant.

The term "cancer" or "malignant neoplasm" refers to a cell that displays uncontrolled growth, invasion upon adjacent tissues, and often metastasis to other locations of the body. The cancer can be a sarcoma, lymphoma, leukemia, carcinoma, blastoma, or germ cell tumor. The cancer can be an epithelial cancer (carcinoma) of a vital organ, such as the pancreas, liver, lung and gut.

The term "C-RC" cell is used herein to refer to a cancer cell capable of cancer propagation. The term includes stem cells, progenitor cells, or transit amplifying (TA) cells for example, VSEC, SDEC and SCEC as described herein.

A "C-RC-specific antigen" is an antigen presented by C-RC cells (e.g., via MHC class I molecules) that is not presented by normal, non-tumor cells.

"VSEC" (very small epithelial cell) is used herein to refer to a subset of "C-RC" cells.

"SDEC" (small dense epithelial cell) is used herein to refer to a second subset of "C-RC" cells, distinguishable from VSEC.

"SCEC" (small cuboidal cell) is used herein to refer to a third subset of "C-RC" cells, distinguishable from VSEC and SDEC.

The term "vector" or "construct" refers to a nucleic acid sequence capable of transporting into a cell another nucleic acid to which the vector sequence has been linked. The term "expression vector" includes any vector, containing a gene construct in a form suitable for expression by a cell (e.g., operatively linked to a transcriptional control element).

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "transduction" "transformation" and "transfection" mean the introduction of a nucleic acid, e.g., an expression vector, into a recipient cell including introduction of a nucleic acid to the chromosomal DNA of said cell.

The term "confluence" refers to the percent coverage of a cell culture dish or flask by cells. "100 percent confluency" means that the dish is completely covered by the cells. "50 percent confluency" means roughly half of the dish is covered and there is still room for cells to grow.

The term "serum free" refers to cell culture using culture medium that does not contain animal serum or plasma. In some embodiments, the serum free medium is chemically defined. "Chemically defined" means that all of the chemical components in the culture medium are known. In certain embodiments, the medium contains a low level or is substantially free of growth factors. If a growth factor is present, it is preferably less than about 10 ng/ml, more preferably less than about 5 ng/ml, e.g., about 1 ng/ml.

II. Methods and Reagents for Targeting C-RC-relevant Antigens

A. Formation of TCR Constructs Targeting C-RC-relevant Antigens

Methods for producing recombinant T cell receptors (TCRs) are disclosed that can be used to prepare therapeutic T cells for adoptive cell therapy (ACT). In preferred embodiments, the TCRs target antigens that are presented by the C-RC cells of the tumor. Therefore, some embodiments of the method involve first preparing an enriched population of C-RC cells from a tumor. Once enriched, the cells may be used to identify C-RC-specific antigen(s). In addition, the cells or the antigen may be used to prepare $CD8^+$ T cells reactive to the C-RC-specific antigen(s). In some embodiments, these reactive T cells are expanded and used in ACT. In preferred embodiments, TCRs from the reactive T cells are cloned into expression vectors that may be transduced into CD8 T cells for ACT.

The disclosed methods can be used to prepare a panel of TCRs. In these embodiments, a patient's tumor biopsy is assayed for tumor antigens and matched to the appropriate TCRs in the panel, which are then transduced into the patient's T cells for use in ACT. The method may also be used to identify new TCRs that effectively target the subject's tumor C-RC cells.

1. Development of TCR Constructs Against Novel C-RC-relevant Targets a. Cultivate C-RC Cells The first step in developing a TCR construct that targets a unique C-RC-specific antigen is the collection of a tumor sample from a patient or donor. The tumor is preferably typed and staged. The tumor sample is cultured under conditions suitable to expand the C-RC cells from the tumor cells that cannot propagate the tumor. In preferred embodiments, tumor samples and normal tissues are selectively cultivated under serum-free, defined conditions that permit cell and tissue response which include autocrine and paracrine signaling between cells within the tissue explant and later, between cells on the culture dish drive cell behavior and growth. It is believed that these stringent conditions of the culture foster activation of a regenerative response where outgrowths of small epithelial cells from the explants contain the cancer's regenerative cells (C-RC). These populations or subsets of cells that grow out of the tumor tissue as a result of a regenerative or stress-induced explant system response would more accurately recapitulate the cancer-initiating cell subset. This would allow more accurate identification of markers or antigens that would resolve the tumor completely.

The emerging small epithelial cells may be further purified by passing the cells into serum-free, preferably chemically defined conditions. The growth factor-poor, chemically-defined conditions induce a stress response in differentiating and differentiated cells, but permit C-RC cells to propagate. It is believed that responses within the tissue initiate the regenerative response with the initiation of stress signaling, to stimulate regeneration as well as the removal of suppressive signaling exerted by healthy mature tissue and stromal cells. For example, an initial burst of C-RC expansion can be seen within the first week, even when the large, mature epithelial cells are still healthy and slowly proliferating. Once the differentiated cell population becomes quiescent, significantly compromised or ultimately depleted through apoptosis, additional C-RC cells become activated, enter the cell cycle and start dividing with increasing rapidity seen as additional bursts of small cell proliferation. In both instances, small cell expansion then continues independent of close association with the explanted tissue or mature cells; the cell expansion is sufficient when a sufficient cell density is reached. The stress response that initiates this selection process for the C-RC cells may be induced through a variety of means, for example, by inducing the apoptosis and/or necrosis of the more mature cells from the bulk of a tumor tumor and stromal cells. In some embodiments, the medium contains cAMP elevating agents, such as cholera toxin and foreskolin, preferably at a concentration of 9 ng/ml) to support sustained G protein signaling and energy metabolism during rapid outgrowth of the C-RC. Furthermore, elevated cAMP may also inhibit the proliferation of more mature tumor and stromal cells. Additional means to further enhance selective pressure and ability to identify and capture the C-RC can be incorporated. The culture medium may also be designed to inhibit cell-cell adhesion to limit the formation of three dimensional structures more apt to promote tumor differentiation, which will re-establish inhibitory signaling on C-RC regeneration. In addition, conditions of low cell adhesion promote C-RC population expansion across the culture surface so that the cells can be identified (morphologically by their small size, proliferation and active colony expansion) and captured. Calcium can be present in the culture medium at a concentration preferably less than about 1 mM, e.g., between about 0.001 to about 0.9 mM, including about 0.01 to about 0.5 mM. Low calcium is the preferred method to limit cell adhesion and promote expansion of the C-RC population out onto the culture surface. Still in some embodiments strontium chloride is added as a cation substitute to support cation-dependent cell functions other than cell adhesion. A low calcium environment combined with the chemically-defined culture medium and minimal concentration of growth factors causes the differentiated cells to divide more slowly, in most cases, to stop dividing with continued time in culture, eventually causing those cells to undergo apoptosis resulting in a population of C-RC left within the culture. in another embodiment, the medium may contain nitric oxide which is known to inhibit cell adhesion and to disrupt cell-matrix interaction. Alternatively or in addition, tumor necrosis factor-alpha (TNF-α), interleukin 1-beta (IL1-β), and interferon-gamma (IFN-γ) can be added to stimulate nitric oxide-induced apoptosis. The cells also may be cultured in diluted hydrocolloid, dextran, or similar material to disrupt cell adhesion and to disfavor the survival of more differentiated cells.

Figure 3:
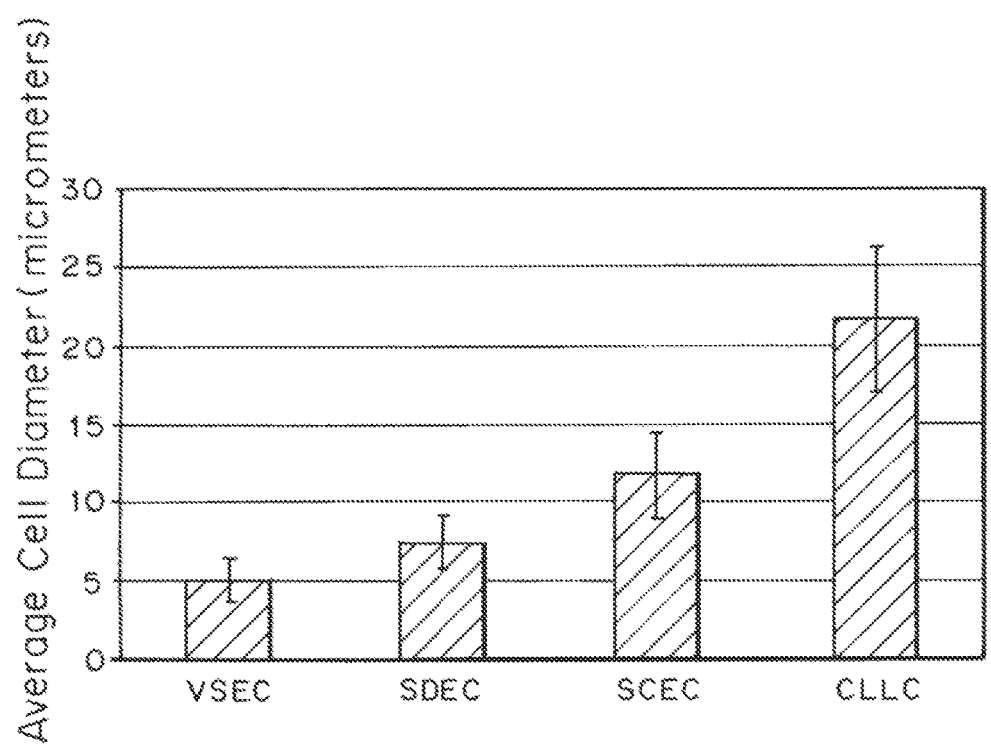
FIG. 3 is a graph of the average sizing data for the C-RC populations derived from two different samples and types of ovarian carcinoma. The C-RC of ovarian cancer manifested as a small cell population that emerged and expanded under primary regenerative conditions. This population consisted of a what appeared to be a lineage of small epithelial cells consisting of an observed progression of very small epithelial cells (VSEC), small dense epithelial cells (SDEC), and small cuboidal epithelial cells (SCEC). This C-RC population was in contrast to much larger non-expanding colonies of cells close to and under the explanted tissue with cell line-like morphologies commonly reported for ovarian cancer cell lines (CLLC). Sizing was done using a Nikon microscope and software. Normal human epithelial progenitor cells will generally range from 9-14 microns.

It is understood that because the tumor initiating cells of the cancer may arise from cell compartments at different stages of differentiation, i.e., tumor initiating cells arising from the stem, progenitor or transit amplifying cell compartments, C-RC cells of interest may have slightly different character and exhibit variations in morphology depending on the cancer type, stage and cell compartment origin. They are distinguished from mature cells and stromal cells in that they are significantly smaller than mature tumor cells or stromal cells (an example of relative size differences seen in ovarian cancer C-RC is shown in FIG. 3) and most preferred, are identified by their selective stimulation under stringent, chemically-defined conditions, exhibiting a burst of proliferative activity and rapid expansion in contrast to the quiescent and apoptotic mature cells and stromal cells within about 7-14 days in primary culture. Following the identifying burst of cell expansion, the C-RC cells can be isolated manually from an explant culture for further processing, or the explant cell culture described herein can be combined with known technology for isolating cells of interest from a cell culture, for example, micro-dissection technology such as laser capture micro-dissection (Mustafa, et al., *Methods Mol. Biol.*, 806:385-92 (2012).

In preferred embodiments, a substantially pure population of C-RC cells near confluence is produced by one or more passaging steps. For example, in some embodiments, the cells are cultured to a confluence of 60% to 95%. The purity of the C-RC cell population can be confirmed by a small size distribution and a high plating efficiency upon further passage. A normal human regenerative cell population from epithelia (consisting primarily of progenitor cells) will have a size distribution in the range of 9-14 microns and will also exhibit a high plating efficiency upon passage. In preferred embodiments, the C-RC cell population in primary and passaged cultures contains between 51% to 100% C-RC cells, preferably between 60%, 70%, 80% to 100% C-RC cells, even more preferably between 90% to 100% C-RC cells.

The primary and/or the purified passaged C-RC cell population is preferably tested for ability to form tumor tissue, including the generation of more mature tumor cells if applicable. This can be accomplished by culturing the cells under defined, differentiating, preferably organotypic culture in vitro and/or implantation of the cells into immunocompromised mice. In preferred embodiments, tumor propagation capacity of the C-RC cells is confirmed both in vitro and in vivo. If positive for tumor formation in vitro and/or in vivo, the cells are confirmed as a C-RC population of the cancer. Further passage in chemically defined conditions can be used to test for potential epithelial-mesenchymal transition as well as further instability and clonal selection within the C-RC cell population. For example, low-density passage of the small C-RC population derived from ovarian cancer onto collagen-coated plates in chemically-defined medium plus 10 ng/mL EGF changes small epithelial cells to a small but mesenchymal cell-like phenotype, which has been associated with metastatic potential.

b. Identify Reactive T Cells

The isolated C-RC cell populations are then used as sources of antigen. In some embodiments, the C-RC cells are treated with interferon-γ to enhance expression of HLA-peptide complexes. The C-RC cells are then mixed with isolated $CD8^+$ T cells to identify reactive T cells. The $CD8^+$ T cells can be isolated from either normal or cancer donors. The CD8+ T cells are preferably HLA Class I-restricted $CD8^+$ T cells from one of three sources. The preferred source is selection via Fluorescence Activated Cell Sorting (FACS) of whole lymphocyte populations from donors in remission from the primary indication due to the presumed higher frequency of reactive T cells within this patient population. Other sources include whole lymphocyte populations from normal donors and Tumor Infiltrating Lymphocytes (TIL) from tumor biopsy samples. The latter sources are alternative options to yield significant numbers of reactive T cells.

The CD8+ T cells reactive to antigens presented by the C-RC cells are isolated using standard protocols. The enzyme-linked immunospot (ELISPOT) assay has become a widely employed method for quantification of antigen-reactive T lymphocytes. In some embodiments, activated T cells are detected via a dual stain cell sorting protocol that detects cells bound to the fluorescently labeled multimer in conjunction with an intracellular stain for the cytokine Interferon-γ, indicating that the cell was activated by the recognition of the TCR-multimer complex.

In some embodiments, an intermediate step is added between initial lymphocyte isolation and the selection method where an in vitro activation protocol selects for CD8+ T cells that are reactive to appropriately presented peptide antigen in the context of patient-relevant HLA molecules. This may be accomplished using one or more of a panel of engineered antigen presenting cells (APC) stably expressing one or more surface HLA types with at least one of those HLA types in common with the donor lymphocyte sample. These engineered APC also express, either endogenously or as a genetically modified enhancement, one or more costimulatory molecules and one or more adhesion proteins which aid in efficient antigen presentation to CD8+ T cells. The APC are pulsed overnight in a multi-well format with one or more peptides derived from the algorithm analysis used to produce the synthetic multimers. By pulsing with multiple peptides per replicate well set, one can perform initial screening of a large number of candidate peptides to narrow the field of hits and then through a subsequent round(s) isolate the peptide of choice which gives the strongest reaction. Several possible analytes can be used to discern lymphocyte reactivity in this in vitro format including, but not limited to, IL-2, IFN-γ, or candidate proteins indicative of CD8 effector function such as perform or granzymes. In some instances CD8+ T cells can be preselected through FACS sorting or magnetic bead separation systems from broader populations, primarily when starting material cell number is not a limiting factor, as this would add to the specificity of the screening outcome.

Figure 2A:
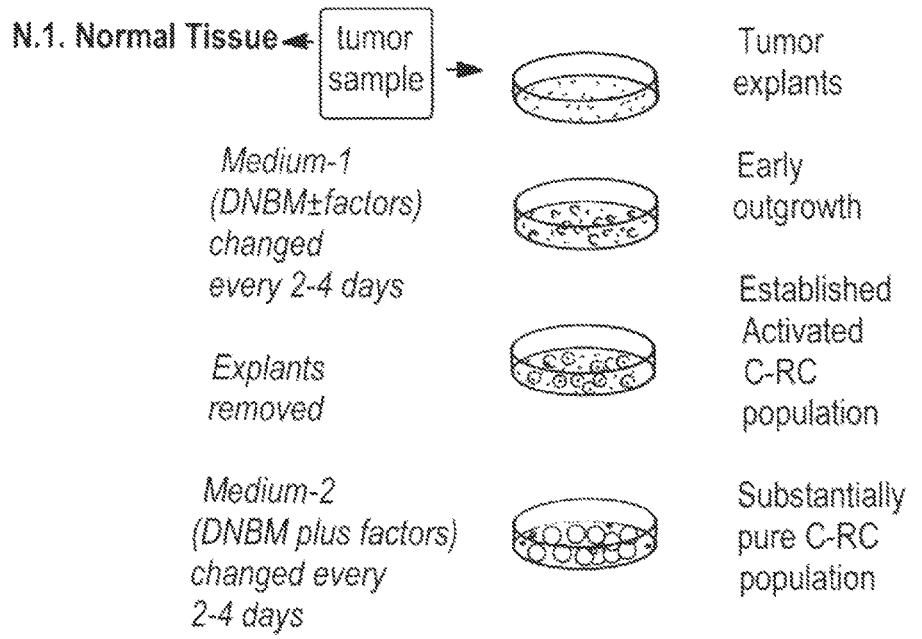
FIGS. 2A and 2B are flow charts depicting a process for identifying C-RC antigens for TCR selection and cloning using subtractive proteomics.
Figure 2A:
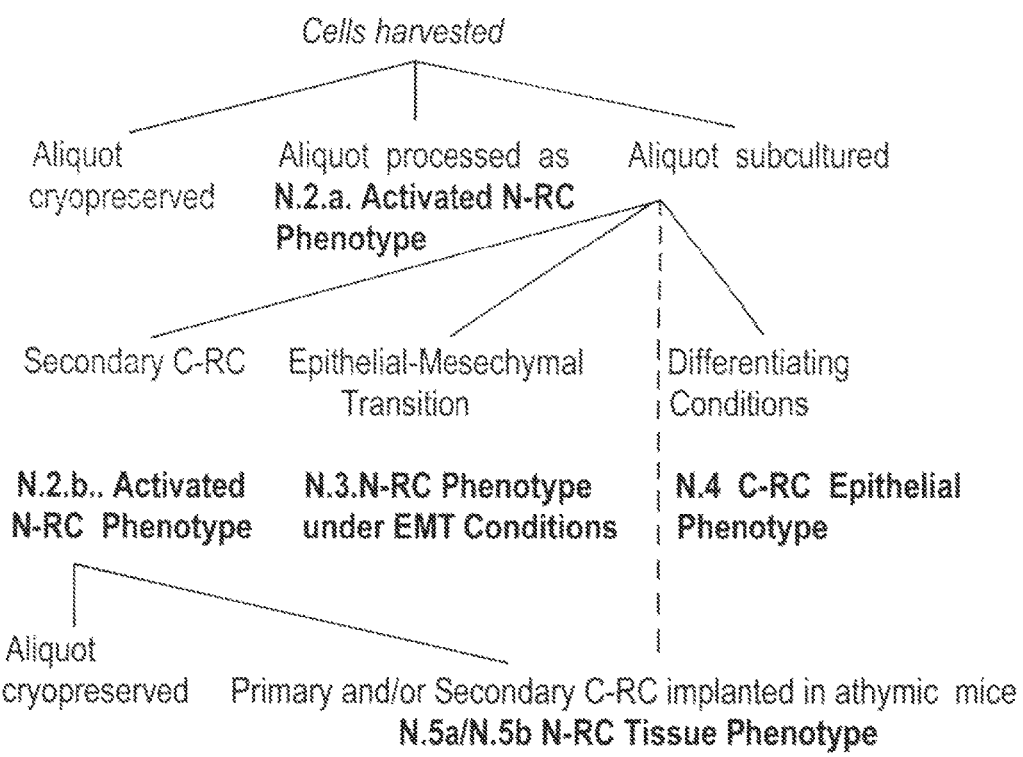
Figure 2A:
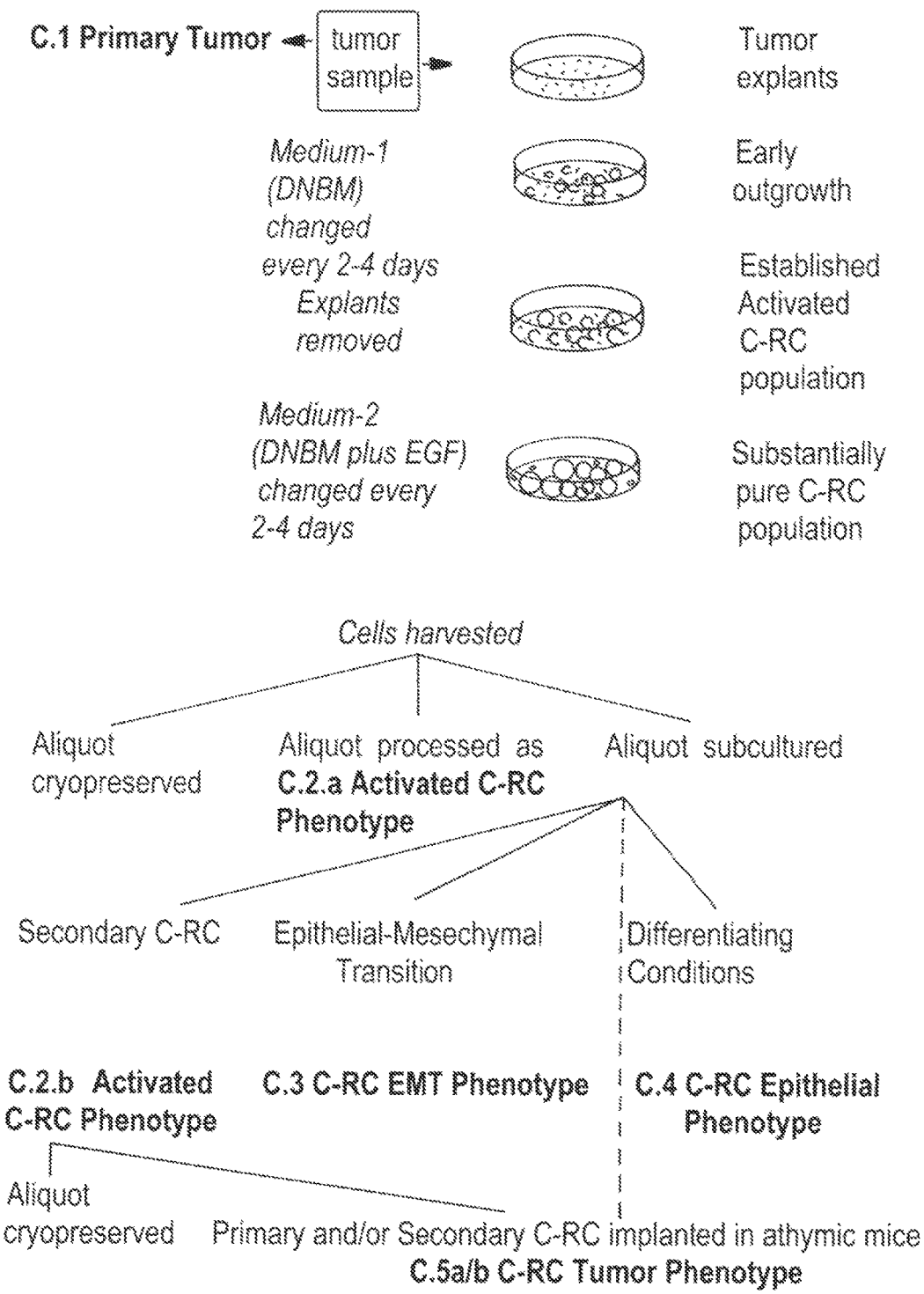
Figure 2B:
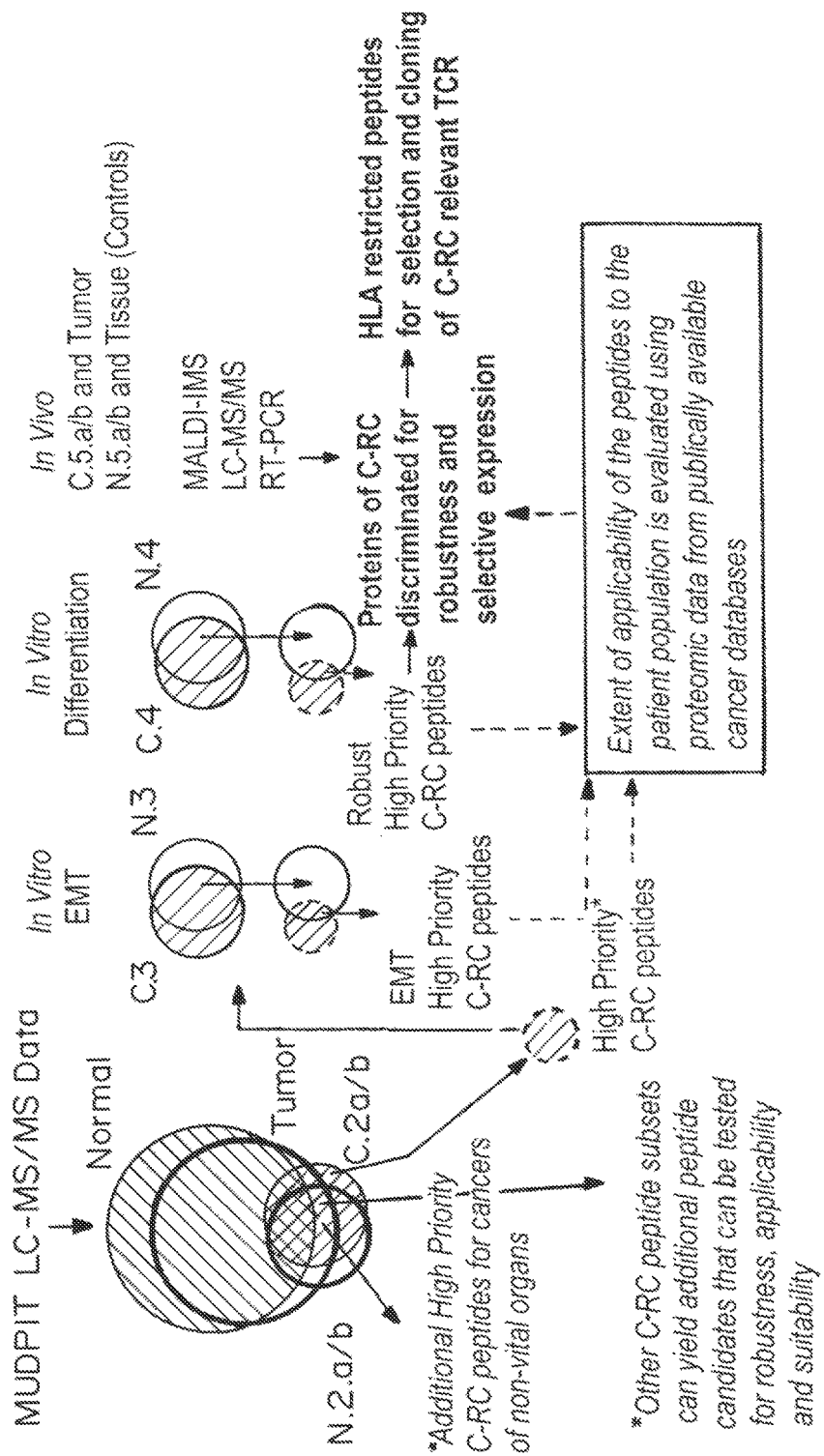

In another embodiment, peptide digests of C-RC and its derivatives are subjected to Multi-dimensional Protein Identification Technology (MUDPIT) or similar technology to identify proteins of the C-RC (FIG. 2B). These targets are then refined and prioritized by successive subtractive analysis (FIG. 2B) to arrive at sets of prioritized protein targets that identify novel markers that can be used for immune targeting of the C-RC population(s) within tumors. HLA matched peptides of the identified protein targets are constructed for TCR selection using the SYFPEITHI algorithm. Sequences are selected to encompass the major HLA types within the population and are used to construct multimers for presentation of the peptide antigens to T cells from tumors, patient T cells, or normal donor T cells. TCRs from selected T cells are then cloned.

c. Clone T Cell Receptors (TCR)

The TCRs of C-RC cell reactive CD8+ T cells may be isolated and cloned into a vector, such as an expression vector using routine methods. In preferred embodiments, RNA from the reactive T cells is subjected to first strand cDNA synthesis and RT-PCR to clone full length TCRa chain and TCRβ chain transcripts for the selected reactive T cells. For example, the method described in Birkholz, K. et al. *J Immunol Methods*, 346(1-2):45-54 (2009)) utilizes a modification of the SMART cloning method established by Zhu, Y. Y., et al. *Biotechniques*, 30(4):892-7 (2001), which allows cloning of full-length transcripts even when full sequences are unknown by attaching a known sequence to the 5' end. The resulting amplified full length TCRa and TCR13 chains may then be subcloned into a standard cloning vector or directly cloned into an expression vector suitable for T cell transfection.

The resulting expression vector is then preferably tested for functional expression. This testing can be performed preferably using naïve peripheral blood T cells or alternatively using a transfection permissive cell line such as one of the many variants of the Jurkat T cell line. Functional expression testing can encompass several test methods including: (1) flow cytometric analysis for TCR surface expression, (2) flow cytometric analysis for specific TCR binding to fluorochrome-labeled multimeric synthetic HLA/peptide complexes, and (3) functional assessment via transduction of peripheral blood lymphocytes and stimulating in vitro with peptide-pulsed, HLA-matched APC and screening for IFN-γ production using standard enzyme-linked immunosorbent assay (ELISA) kits.

Once expression and functional characteristics of the selected TCR expression constructs is satisfactorily established larger scale production of optimally titered expression vector can be produced, facilitating product scale-up and clinical development.

In preferred embodiments, CD8+ T cells are transduced with the cloned TCR expression vector and tested for the ability to respond to an expressed HLA-restricted peptide complex. Positive TCR constructs are preferably expanded, and frozen aliquots of these constructs may be added to a banked TCR expression panel.

d. Sequence and Use of C-RC-specific Antigen

If the T cells are selected using complex antigen presentation (FIG. 1), the peptide associated with the reactive TCR is sequenced for protein identification and probes and/or antibodies are made against the identified protein. If the peptide antigen is determined prior to T cell selection using successive proteomic subtraction (FIG. 2B), probes and/or antibodies are generated against peptides from the identified protein. This antigen may be used to produce molecular probes and/or antibodies that are useful for screening tumors. For example, if a patient's tumor is shown to express the C-RC-specific antigen, the corresponding TCR clone may be useful to treat that patient by ACT.

In preferred embodiments, the probe or antibody is used to confirm the presence of the C-RC-specific antigen and the ability of the TCRs to target tumor propagation and progression. In some embodiments, the presence of antigen is confirmed in 1) serum-free C-RC cell cultures, 2) organotypic cultures, 3) tumors from immunocompromised mice, 4) human tumor samples, or combinations thereof. If expression of the antigen is maintained in one or more of these conditions, the TCR is deemed capable of targeting tumor propagation and progression.

Therefore, in some embodiments, TCR constructs against unknown C-RC-specific antigens are produced by the following steps:
1. Tumor samples of a cancer type and stage are obtained from donors.

2. Explant outgrowths of the tumor biopsies and corresponding normal tissues are selectively cultivated under serum-free conditions that foster activation of a regenerative response where outgrowths of epithelial cells from the explants contain prospective C-RC cells.
3. The outgrown cells are passed into serum-free conditions that yield a substantially pure population of prospective C-RC cells near confluence, confirmed by a high holoclone colony forming efficiency upon further passage.
4. Progenitor/progenitor-like C-RC populations are tested for tumor propagation and progression by culture of the population in organotypic culture in vitro, and/or implantation of the cells into immunocompromised mice, preferably both. If positive for tumor formation in vitro and/or in vivo, the cells are confirmed as a C-RC population of a cancer. Further passage in stringent serum-free conditions can be used to test for potential epithelial-mesenchymal transition as well as further instability and clonal selection within the progenitor/progenitor-like population.

The isolated C-RC cell populations are used as sources of antigen. C-RC cells are treated with interferon-γ to enhance expression of HLA-peptide complexes and mixed with isolated $CD8^+$ T cells from either normal or cancer donors. The $CD8^+$ T cells reactive to antigens presented by the C-RC cells are isolated using standard protocols (FIG. 1). Alternatively, the TCR are selected using multimer-presented peptides from novel protein targets that have been identified and prioritized through selective and successive proteomic analysis of C-RC, normal cell and tissue and tumor proteomes (FIG. 2B).

5. The T cell receptors (TCR) are cloned from the isolated reactive T cells
6. The associated peptide is sequenced through a combination of selective and successive proteomic analyses to identify the C-RC antigen and molecular probes and antibodies can now be made for screening purposes.
7. The presence of antigen is confirmed in serum-free C-RC cell cultures, differentiating cultures, organotypic cultures, tumors from immunocompromised mice and human tumor samples. If expression of the antigen is maintained, the TCR is deemed capable of targeting tumor propagation and progression.
8. Normal T cells are transduced with the cloned TCR construct and tested for their ability to respond to expressed HLA-restricted peptide complex.
9. Positive TCR constructs are expanded and frozen aliquots are added to a banked TCR expression panel.

2. Development of TCR Constructs Against Known Cancer Markers and Putative C-RC-relevant Targets Methods for producing TCR constructs against known cancer markers are also disclosed. As above, the method generally involves first obtaining an enriched population of C-RC cells from the cancer. Expression of the cancer markers and the ability of the TCRs to target tumor propagation and progression may then be confirmed. In some embodiments, the presence of antigen is confirmed in 1) serum-free C-RC cell cultures, 2) organotypic or other cultures capable of causing differentiation such as epithelial-mesenchymal transition 3) tumors from immunocompromised mice, 4) human tumor samples, or combinations thereof by direct labeling and/or by analysis of their respective proteomes (FIG. 2B). If expression of the antigen is maintained in one or more of these conditions, the TCR is deemed capable of targeting the cells capable of propagation and progression.

In preferred embodiments, a peptide digest of the target tumor tissue or C-RC proteins is prepared. Peptide target preparations may be subjected to successively refined proteomic selection through established chromatographic, mass spectrophotometric, and analysis algorithms to arrive at a refined pool of C-RC peptides (FIG. 2B).

The successively refined peptide targets are then presented to $CD8^+$ T cells, e.g., isolated from normal or cancer donors or tumor TIL. As above, TCRs are then cloned from reactive $CD8^+$ T cells, Normal T cells may then be transduced with the cloned TCR construct to test its ability to respond to expressed HLA-restricted peptide complex. Positive TCR constructs may then be expanded, and frozen aliquots are added to a banked TCR expression panel. Therefore, in some embodiments, TCR constructs against known cancer markers and putative C-RC-specific targets are produced by the following steps. C-RC populations are derived as in 1.1-3 above.

The presence of putative antigen is confirmed in serum-free C-RC cell cultures, organotypic cultures, tumors from immunocompromised mice and human tumor biopsies. If expression of the antigen is maintained, the antigen is deemed capable of targeting tumor propagation and progression.

A peptide digest of the target tumor tissue or antibody-selected protein antigen is prepared.

Peptide target preparations are subjected to successively refined proteomic selection through established chromatographic, mass spectrophotometric, and analysis algorithms to arrive at a refined pool of C-RC peptides.

The successively refined peptide targets are presented to CD8+ T cells isolated from normal or cancer donors and tumor TIL.

TCR are cloned from reactive CD8+ T cells.

Normal T cells are transduced with the cloned TCR construct and tested for its ability to respond to expressed HLA-restricted peptide complex.

Positive TCR constructs are expanded and frozen aliquots are added to a banked TCR expression panel.

The following are specific examples of methods to identify, analyze and use these methods.

Confirmation of the Tumor Propagating Population

The progenitor/progenitor-like population is subjected to three different conditions to confirm the tissue/tumor propagating capability, to generate additional proteomic data for subtraction, and to confirm marker expression:

The progenitor or progenitor-like C-RC population is cultivated in DNBM plus cholera toxin. Cultures are harvested at 60-90% confluence. The harvested cells are used for marker analysis, genetic or proteomic analysis with confirmation of the progenitor and progenitor-like character of the population by passing a portion of the population into a defined colony forming efficiency assay consisting of low cell density plating in DNBM, cholera toxin, EGF and BPE and/or a feeder cell colony forming assay with DNBM plus 1-10% serum. The proportion of holoclones measures the proportion of progenitor cells in the cell suspension undergoing analysis.

The substantially homogeneous N-RC or C-RC population is passed to in vitro conditions that support organogenesis, i.e, 3-dimensional tissue formation and differentiation. The protocols vary depending on the origin of the cells but may consist of adding factors such as FGF and/or HC to DNBM culture with EGF in high calcium (≥1 mM) DNBM to promote cluster formation. Protocols may employ an extracellular matrix such as a collagen lattice containing normal fibroblasts or tumor stromal cells, where the epithelial cells are plated on or below a contracted collagen lattice formed on a porous membrane or suspended within the collagen gel or collagen lattice containing stromal fibroblasts, where they are cultured submerged in DBNM or at a moist or dry air-liquid interface as appropriate for the type of epithelium being cultured. Alternatively the cells are plated on or within ≤1 mm layer of Matrigel and fed with DNBM supplemented with cholera toxin, EGF, HC, HGF, IGF-1 and/or FGF as needed The organotypic condition supports progenitor differentiation to transit amplifying cells and terminal maturation in a tissue-like manner. The formation of cell clusters in or on Matrigel and their ability to develop tissue structure, even though it may be abnormal in the case of cancerous cells, is also used as a confirming assay for progenitor and progenitor-like function.

The progenitor or progenitor-like C-RC population is implanted into immunocompromised mice and allowed to develop into tumors in a method such as that described by Bankert, et al. *PLoS ONE* 6(9):e24420 (2011).

If a cell population generated by the progenitor activation protocols is capable of continued growth under defined conditions, the cells are challenged by continued passage and colony forming efficiencies monitored under defined conditions to determine lack of stability and further clonal selection of the population. This is used to determine marker expression on cells possibly capable of progression.

Organotypic culture is used to determine the differentiation capacity of the cell population. If the progenitor or progenitor-like C-RC cells are capable of differentiation, it will be seen in the organotypic culture. The degree of hyperproliferation, tissue organization and heterogeneity compared to normal cells is used to determine whether transit amplifying cells are capable of differentiation or are merely contributors to tumor bulk or a tumor propagating population that must be targeted by the therapy. Marker expression is determined by immunohistochemistry and/or in situ PCR and/or MALDI-IMS.

Tumor formation in immunocompromised mice is used to estimate relative in vivo tumorigenic capacity as well as to generate tumor samples for marker expression analysis. Morphology and tumor heterogeneity is compared to data obtained from organotypic and progenitor activation protocols to confirm that the cells of the progenitor-like population are most likely responsible for tumor propagation and progression. A high colony forming efficiency, hyperplastic, disorganized tissue with low heterogeneity in organotypic culture and multiple tumors in immunocompromised mice will characterize a highly aggressive, advanced cancer where the TCR panel must target all cells of the population, one or more engineered receptors targeting the progenitor and one or more targeting the transit amplifying progenitor-like population. A single target may address both compartments but overlap is not necessary. A low colony forming efficiency, hyperplastic but heterogeneous tissue with signs of tissue-specific differentiation in organotoypic culture and fewer tumors in immunocompromised mice will characterize a tumor where the tumor propagating cells of the cancer are still confined to a progenitor compartment. For therapy, preferably two or more markers of the TCR panel must target this progenitor subpopulation. A third scenario is that the abnormality is derived in the transit amplifying cell population, where a progenitor cell population is not required for continued growth and progression of the tumor. This will manifest as high colony forming efficiency because of progenitor-like cells but the character of the colonies and their expression of markers will differ from a population predominated by progenitor cells. Cell size and colony organization with respect to marker expression will differ and the colonies will exhibit gene and protein expression profiles that contain features of differentiation as well as progenitor cells. The stress of defined colony growth will also foster EMT in susceptible populations, which may or may not be abetted by the addition of small amounts of TGFβ or IFN-γ. Testing the population in differentiating organotypic culture determines the extent of inherent differentiation capability, and confirms the persistent expression of a putative target. In vivo transplantation gives a measure of the tumorigenicity of the progenitor-like C-RC population in a more complex environment with stromal and vascular influences and yields tumors that can be compared to the organotypic cultures, active C-RC and native tumor samples (FIG. 2B).

In all cases, high priority targets should be able to sufficiently discern abnormal C-RC from N-RC. N-RC populations in the three conditions are used for comparison of marker expression (FIG. 2A). Ideally, the cancer expresses a mutant form of a protein and the TCR is engineered to preferentially recognize the mutant peptide. Alternatively, the cancerous progenitor population over expresses a developmental antigen such as a carcinoembryonic antigen so that a TCR is engineered to have a high affinity to preferentially recognize the high level of abnormal expression, leaving the normal progenitor unrecognized. Alternatively, in a clean slate approach, the engineered T cells are also engineered with a suicide gene allowing removal of the engineered T cells upon tumor regression. Removal of the reactive T cells allows normal progenitors to repopulate the organ with transit amplifying cells that mature into normal functional parenchyma, which then serve as natural barriers to recurrence.

Target Selection Starting from Known Cancer Markers, Established or Putative and the Production of Corresponding TCR Constructs One can draw from known antigens preferentially or exclusively expressed in or on cancerous tissues, but more specifically the C-RC of the cancer within those tissues. Numerous target markers have been identified through differential genomic and/or proteomic analyses of normal versus cancerous tissues. To exploit these findings preferential or unique expression of the marker of interest, either expressed on the surface of target cells or intracellularly is determined from the proteomic data (FIG. 2B) and may be confirmed through standard flow cytometric, immunocytochemical or MALDI-IMS methods. Also through examination of expression, it is determined that the antigen is therapeutically viable if its expression is maintained within the C-RC population upon expansion via tissue culture conditions specified in Examples 1-3 and whose expression remains relevant in in vivo modeling systems which enable immunologic examination of their relevance. Several highly versatile immune-compromised animal strains that express a variety of human immune markers in compartmentally valid patterns can be used for in vivo testing. These animals allow Human Leukocyte Antigen (HLA) matched and tissue specific expansion of selected tumor C-RC populations in vivo under conditions that enable their examination from both oncologic and immunologic perspectives.

The development of TCR panel candidates from known antigens starts with peptide sequences from known target antigens expressed exclusively or predominantly on the C-RC populations of target indication cancer samples that have been pre-screened for confirmation of target antigen expression by the presence of corresponding peptides in the proteomic data from the samples, Flow cytometric or molecular mRNA expression profiling or all methods. Specifically, proteomic data is obtained by analysis of peptide digests using Multi-Dimensional Protein Identification Technology (MUDPIT). Flow cytometry is used to detect proteins expressed on the cell surface as well as those expressed cytolplasmically via standard methods involving membrane permeabilization and fixation. An array of fluorochome-conjugated monoclonal antibodies enables detailed detection of multiple ligands simultaneously increasing detection specificity and down-stream information content for the C-RC population. Expression at the level of mRNA expression is accomplished through custom quantitative reverse transcriptase polymerase chain reaction (qRT-PCR) arrays, which allow rapid and quantitative point-in-time analysis of mRNA species of interest along with mRNA species of related or pathway-associated members of the similar protein families.

Established algorithms (SYFPEITHI prediction algorithm score of 21 or higher) are used to screen overlapping peptide sequence libraries generated from known whole target antigen amino acid sequences that efficiently bind within the HLA Class I molecule cleft formed by the α1 and α2 domains of the HLA sequence and also present an efficient binding target for specific amino acid residues within the CDR3 region of T Cell Receptors specific for that peptide in the context of a particular HLA type (Sethi, et al. *J. Experiment Med* 208(1)91-102 (2011)). Using these algorithms the chosen peptides are used in conjunction with synthetically produced multimers representing a wide variety of HLA types that are loaded with selected peptides and used to detect reactive HLA Class I-restricted T cells from a mixed population of activated T cells. More widely known as tetramers, the variant of multimers being referenced here are commercially available and more sensitive due to higher affinity and higher fluorochrome-to-protein ratios. These multimeric peptide constructs are used to specifically select HLA Class I-restricted $CD8^+$ T cells from one of three sources. The preferred source is selection via Fluorescence Activated Cell Sorting (FACS) of whole lymphocyte populations from donors in remission from the primary indication due to the presumed higher frequency of reactive T cells within this patient population. Other sources include whole lymphocyte populations from normal donors or from Tumor Infiltrating Lymphocytes (TIL) from tumor biopsy samples. The latter sources are alternative options to yield significant numbers of reactive T cells.

Because activation signals resulting from the crosslinking of TCR molecules on the surface of $CD8^+$ T cells by binding the multimeric synthetic proteins generate some cytokine production, activated cells are detected via a dual stain cell sorting protocol that detects cells bound to the fluorescently labeled multimer in conjunction with an intracellular stain for the cytokine Interferon-γ, indicating that the cell was activated by the recognition of the TCR-multimer complex. This provides added assurance that the cells selected are in fact reactive to the tumor antigen in question but is not essential. It is conceivable that the PCR and cloning steps subsequently referred to can be accomplished with as little as one cell.

Alternatively, an intermediate step can be added between initial lymphocyte isolation and any selection method where an in vitro activation protocol selects for $CD8^+$ T cells that are reactive to appropriately presented peptide antigen in the context of patient-relevant HLA molecules. This is accomplished by using one or more of a panel of engineered antigen presenting cells (APC) stably expressing one or more surface HLA types with at least one of those HLA types in common with the donor lymphocyte sample. These engineered APC also express, either endogenously or as a genetically modified enhancement, one or more costimulatory molecules and one or more adhesion proteins which aid in efficient antigen presentation to $CD8^+$ T cells. The APC are pulsed overnight in a multi-well format with one or more peptides derived from the algorithm analysis used to produce the synthetic multimers. By pulsing with multiple peptides per replicate well set, one can perform initial screening of a large number of candidate peptides to narrow the field of hits and then through a subsequent round/s isolate the peptide of choice which gives the strongest reaction. Several possible analytes can be used to discern lymphocyte reactivity in this in vitro format including, but not limited to, Interleukin-2, Interferon-γ, or candidate proteins indicative of CD8 effector function such as perforin or granzymes. In some instances $CD8^+$ T cells can be pre-selected through FACS sorting or magnetic bead separation systems from broader populations, primarily when starting material cell number is not a limiting factor, as this would add to the specificity of the screening outcome.

Figure 4A:
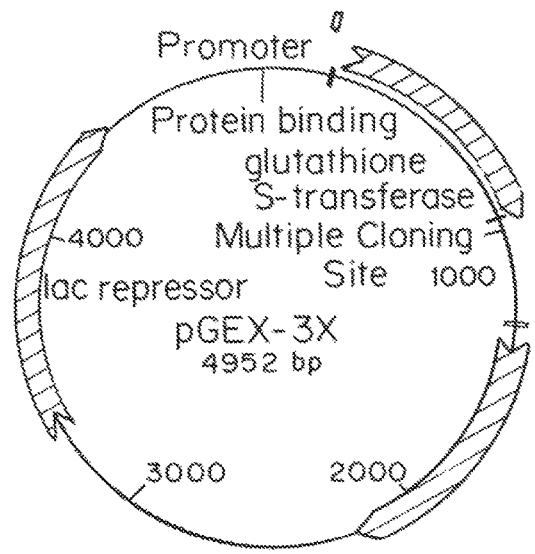
FIGS. 4A and 4B are illustrations of vectors used to clone TCRs. pGEX-3X (4A) and pLent-MULTI (4B).
Figure 4A:
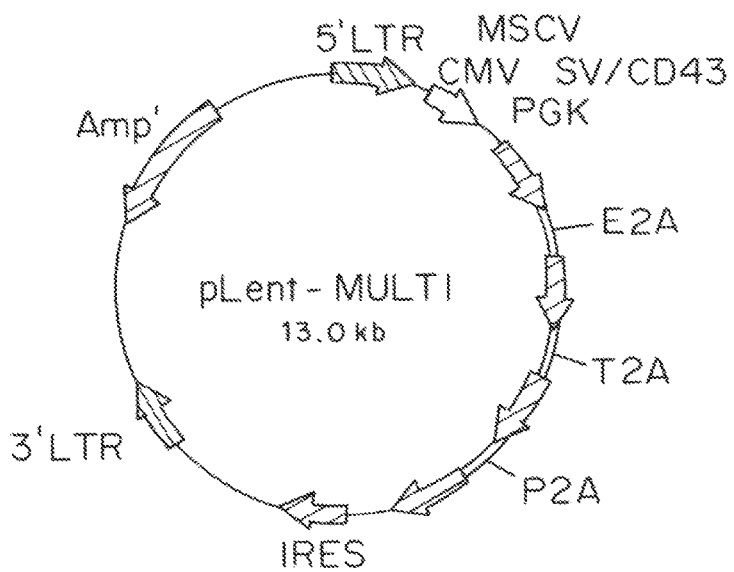
Figure 4A:
Figure 4B:
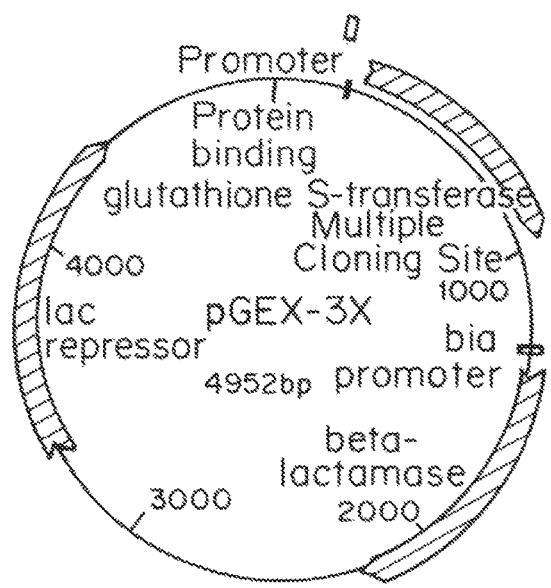
Figure 4B:
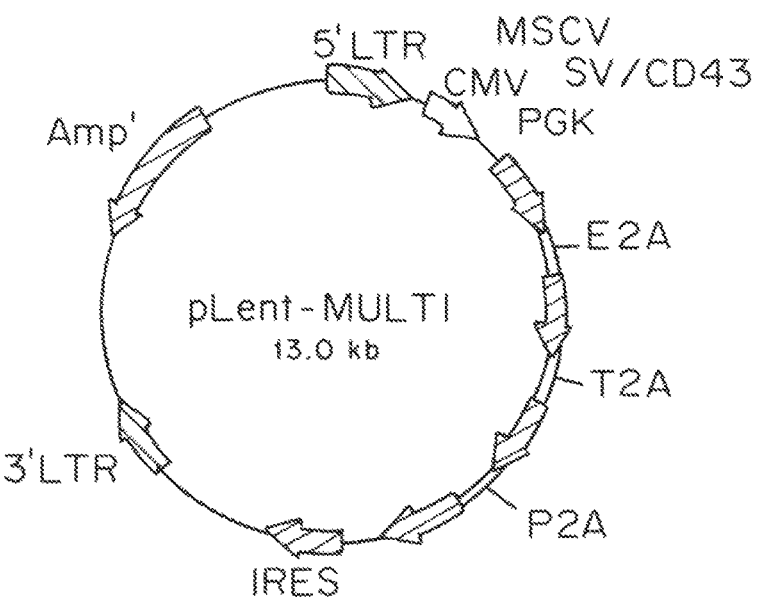
Figure 4B:

Once $CD8^+$ T cell populations have been isolated and identified through the combination of selection and detection systems described above, whole RNA content of the selected cells is subjected to first strand cDNA synthesis and RT-PCR to clone full length TCRα chain and TCRβ chain transcripts for the selected reactive T cells, essentially as described in Birkholz, K. et al. *J Immunol Methods.* 2009 Jul. 31; 346(1-2):45-54 (2009)). This method utilizes a modification of the SMART cloning method established by Zhu, Y. Y., et al. *Biotechniques.* 30(4):892-7 (2001), which allows cloning of full-length transcripts even when full sequences are unknown by attaching a known sequence to the 5' end. The resulting amplified full length TCR α and β chains are subcloned into a standard cloning vector similar to the versatile pGEX vector in FIG. 4A or alternatively can be directly cloned into a polycistronic lentiviral expression vector, such as the one depicted in FIG. 4B, with similar properties to vectors described by Takahashi K and Yamanaka S, *Cell.* 126(4):663-76 (2006) and was further refined for use in T cell receptor expression methods by Jones, S. et al. *Hum Gene Ther.* 20(6):630-40 (2009). Once cloned into lentiviral expression vectors, test lots of packaged virus are produced using one of many commercially available and highly adaptable 293T cell line packaging systems such that viral titers of $>10^7$ Transducing Units (TU) per mL are available for functional expression testing. Functional expression testing can encompass several test methods including: (1) flow cytometric analysis for TCR surface expression, (2) flow cytometric analysis for specific TCR binding to fluorochrome-labeled multimeric synthetic HLA/peptide complexes, and (3) functional assessment via transduction of peripheral blood lymphocytes and stimulating in vitro with peptide-pulsed, HLA-matched APC and screening for Interferon-γ production using standard enzyme-linked immunosorbent assay (ELISA) kits. Once expression and functional characteristics of the selected TCR expression constructs is satisfactorily established larger scale production of optimally tittered virus can be produced facilitating product scale-up and clinical development.

Target Discovery of Novel Antigens and the Production of Corresponding TCR Constructs The method enables the discovery of novel antigens for use as targets of ACT, utilizing samples from typed and staged tumor biopsies of epithelial cancers where subcultures from tumor biopsy and control tissues are enriched for tumor C-RC and normal progenitor subpopulations (Examples 1-2). These cultured subpopulations serve as the basis for confirmation analysis using multiple in vitro and in vivo methodologies including, but not limited to, subculture using differentiation-inducing organotypic culture and behavior of subcultured implants in HLA-transgenic immunocompromised mouse strains with comparison to original biopsy material (Example 3). Therapeutic relevance is partially confirmed through the ability to repeatedly derive nascent tumors in one or more of these models.

The platform for discovery of novel target antigens and the subsequent cloning of tumor-specific TCR begins by combining: 1) validated C-RC populations, verified in vitro and in vivo according to methods described (Examples 1-3) and matching normal progenitor sub-populations for comparison, and 2) sourced protein lysate libraries derived from the above as well as epithelial cancer biopsy samples and samples of physiologically and anatomically matched tissue. This extended protein lysate library ensures preferential and stable expression patterning of proteins and subsequent peptide profiles from original tissue samples through culture-derived tumor C-RC versus normal progenitor subcultures.

To arrive at credible protein targets from the extended protein lysate library, the system employs a combination of selected or combinatorial fractionation chromatography (MUDPIT or alternative technologies, which are known in the art) and global proteomic analysis on matched normal progenitor and C-RC cancer populations to generate proteomic subtraction peptide libraries. From these peptide subtraction libraries amino acid sequences are isolated that are unique to the tumor C-RC cell type and can be sourced back to whole protein targets through standard proteomic analysis tools. The combination of definable ion exchange chromatography and mass spectrometry methods represents global proteomic profiling that permits biomarker discovery based on changes in protein expression levels between matching tumor C-RC and normal progenitor samples at high resolution.

The biomarker discovery through the proteomic subtraction library generates target antigens expressed exclusively or predominantly expressed on the C-RC cell populations. Samples from target indication cancers are pre-screened for confirmation of target antigen expression by Flow cytometric or molecular mRNA expression profiling or both. Specifically, flow cytometry can be used to detect proteins expressed on the cell surface as well as those expressed cytoplasmically. Standard methods involving membrane permeabilization and fixation along with the array of fluorochrome-conjugated monoclonal antibodies enable detailed detection of multiple ligands simultaneously increasing detection specificity and down-stream information content for the C-RC population. Expression at the level of mRNA expression is accomplished through custom quantitative reverse transcriptase polymerase chain reaction (qRT-PCR) arrays, which allow rapid and quantitative point-in-time analysis of mRNA species of interest along with mRNA species of related or pathway-associated members of the similar protein families.

As described in Example 4, algorithm screens are (SYFPEITHI prediction algorithm score of 21 or higher) used to screen overlapping peptide libraries generated from sourced whole target antigen sequences. In the case of Example 5 these target antigens are sourced from the peptide subtraction library methods described above. The selected peptides are predicted to efficiently bind within the HLA Class I molecule cleft formed by the α1 and α2 domains of the HLA sequence and also present an efficient binding target for specific amino acid residues within the CDR3 region of TCR specific for that peptide in the context of a particular HLA type (Sethi D K, et al. *J Exp Med.* 208(1):91-102 (2011)). Peptides chosen via these algorithms are used in conjunction with synthetically produced multimers representing a wide variety of HLA types and are loaded with specific peptides and used to detect reactive HLA Class I-restricted T cells from a mixed population of activated T cells. The combination of selective identification of peptides from subtraction libraries and confirmation of reactivity as described in Example 4 allows isolation and cloning of TCR sequences validated for reactivity to unique target antigens. Tissue and indication-specific whole protein samples provide a rich resource for this screening process and the derivation of a validated TCR panel for ACT.

B. Treatment of a Patient Using the TCR Panel

The disclosed TCR panel of cloned TCRs that target C-RC-specific antigens may be used to treat cancer in a subject by adoptive T cell therapy. The TCR Panel contains a plurality of TCR constructs against multiple antigen targets. In preferred embodiments, a defined set of two or more TCR constructs serve as reagents for patient T cell modification and define the therapy for a given cancer type and stage.

Adoptive T cell therapy using the disclosed TCR panel generally involves first screening a patient's tumor biopsy for the presence of C-RC-specific antigens. In preferred embodiments, a biopsy from the patient's tumor is submitted to a central testing laboratory where it is tested for the presence of C-RC-specific antigens. For example, the tumor biopsy can be assayed using antibodies or probes that specifically bind the C-RC-specific antigen peptides (or expressed nucleic acids as upstream coding surrogates for the peptides) associated with the TCR panel. Patients positive for the presence of a C-RC-specific antigen with corresponding HLA Class I restriction are candidates for the adoptive T cell therapy.

The next step is to obtain CD8$^+$ T cells for further processing. The CD8$^+$ T cells are preferably obtained from the patient, e.g., by lymphapheresis. The T cells are transduced with expression vectors encoding the TCR corresponding to the C-RC-specific antigens detected in the tumor biopsy. In some embodiments, the transduced T cells are expanded using standard cultivation methods to provide sufficient quantities for therapeutic use. The transduced T cells are also preferably quality tested for therapeutic application.

Before reinfusion, lymphodepletion of the recipient is preferred to eliminate regulatory T cells as well as normal endogenous lymphocytes that compete with the transferred cells for homeostatic cytokines. Partial lymphodepletion can be performed using one or more drugs such as, but not limited to, cyclophosphamide and fludaramine.

Once a sufficient quantity and purity of transduced T cells are produced, a therapeutically effective amount of cells are infused into the patient. The remaining engineered T cells may be cryopreserved and banked for future use. In some embodiments, adjuvant therapy is used to increase expression of MHC Class I:peptide complex on the tumor cell surface. Representative adjuvants include cytokines engineered into the therapeutic T cells, alum, inhibitors of methylation, such as DNA methyltransferase (DNMT) or histone deacetylyase (HDAC), and systemic or localized delivery of immune modulating agents such as Interferon-gamma (IFN-γ). The cells are preferably modified to express cytokine, such as IL-12, to enhance T cell response and the immune response at the tumor site. In some embodiments, the cells are transduced with an expression vector encoding a cytokine, such as IL-12. In other embodiments, the vector encoding the TCR further encodes a cytokine, such as IL-12.

Therefore, in some embodiments, engineered T cells are used for adoptive T cell therapy using the following steps.

T cells from candidate patients are obtained by lymphapheresis and sent to a central facility for processing.

The patient's immune system is prepared by partial lymphodepletion using one or more drugs such as, but not limited to, clyclophosphamide and fludarabine.

The CD8+ T cells are isolated from the collected T cell sample and transduced with the set of TCR viral constructs and a cytokine to enhance T cell response.

The transduced T cells can be expanded if necessary for effective dosing, quality tested and returned to the clinic where they are infused into the patient. Aliquots of the engineered T cells are cryopreserved and banked for future use.

The following is a detailed example of how a patient can be treated using this method.

Use of the TCR Panel in ACT for the Treatment of Cancer

The TCR constructs developed from known and novel cancer antigens form a TCR panel of therapy-ready constructs that can be selected for their suitability to treat a certain type and stage of a cancer. A TCR construct may be suitable for more than one type of cancer while others will be type and/or stage specific. All constructs in the TCR panel have been previously validated to be C-RC relevant as described in the preceding examples. The therapy for each cancer type and stage consists of a set of TCR constructs from the panel. Preferably, each set consists of at least two TCR constructs reactive to distinct C-RC-relevant antigens. A kit is provided to an oncology center consisting of a sterile vessel containing transport medium, instructions, a medical questionnaire to collect cancer and treatment history, and an insulated shipment container. Tumor samples are received and tested for presence of the TCR panel antigens and the tumor type and stage is confirmed. Patients positive for at least one and preferably multiple antigens in the therapeutic set of TCR constructs are considered candidates for the therapy. Data on the tumor and the presence of C-RC antigens is reported to the submitting oncologist.

Patient T cells are collected by lymphapheresis and transduced with the set of TCR vectors established for the type and stage of cancer as well as an IL-12 construct. The engineered T cells are expanded, quality tested, and suspensions are shipped back to the treatment facility for infusion. Aliquots are banked at the processing facility for repeat therapy and monitoring purposes, if needed. Patients are infused with the living engineered T cells.

The present invention will be further understood by reference to the following non-limiting examples.

EXAMPLE 1

Derivation of C-RC Populations from Cancer Biopsies of Advanced Cancers and Normal Regeneration-capable Populations (N-RC)

The work flow for the derivation and sampling of C-RC and N-RC is depicted in FIG. 2A.

A portion of each tumor biopsy is minced and plated, evenly spaced, on collagen-coated dishes (1 mg Type I collagen, washed/mL). The dishes are flooded with a nutrient medium that supplies a necessary nutritional base that supports progenitor cell activation preferably consisting of DMEM (calcium-free, without glucose):Ham's F-12 in a 3:1 ratio supplemented with adenine, ethanolamine/phosphoethanolamine, insulin, triiodithyronine, transferrin, selenium and strontium chloride. The medium may also contain hydrocortisone, progesterone and/or EGF. Alternatively, a commercially formulated low calcium (≤1.0 mM) defined base medium demonstrated to propagate normal epithelial progenitor cells from human epidermis or mammary gland may serve as a nutritional base substitute for some cancer types and stages. The Defined Nutritional Base Medium (DNBM) is further supplemented with 9 ng/mL cholera toxin or other suitable cyclicAMP elevating agent such as forskolin. Normal tissues used for comparison will be low in intrinsic regenerative capacity and regenerative activation normally limited in adult human tissue, may benefit from the addition of 1-50 µg/mL bovine or porcine pituitary extract or alternatively, a defined cocktail of additional growth factors including one or more of IGF-1, HGF and/or FGF at 10 ng/mL each. Not every tumor sample or normal tissue will be able to successfully mount the level of autocrine and paracrine signaling needed to activate a regenerative response in a native C-RC population. However, unlike normal tissue, for cancer, the use of animal pituitary extracts or other undefined supplements such as serum or other bodily fluids, for example, ascites fluid, or the use of complex mixtures of growth factors prior to C-RC activation, can confound results by artificially deriving a proliferative cell population that has lost phenotypic fidelity or it can lead to the undesirable survival and proliferation of the non-RC tumor cells and stromal cells resulting in suppression of the C-RC population thereby limiting the burst of regenerative activation necessary for rapid functional identification, greatly delaying or prohibiting altogether their identification and capture. It is understood that inherent genetic instability and malregulation associated with cancer cells can lead to rapid adaptation in vitro (Strauss et al., *PLOSOne*, 6:e16186 (2011)), therefore it is preferable that the C-RC population be derived from endogenous regenerative signaling within or amongst the tumor explant and primary cells as soon as possible to assure fidelity of the response and phenotype, in the correct cell population, most preferably from explanted tissue. For cancer tissue, derivation of the C-RC population is preferably carried out in chemically defined medium with EGF as the only exogenous growth factor or most preferably without any exogenous growth factor supplementation. Expansion of C-RC cultures of some types and stages of tumors may benefit from defined supplementation of one or more growth factors in addition to EGF, once the C-RC population burst is observed and most preferably only after the C-RC have become the dominant population of the culture.

The cultures are left undisturbed for 4-5 days and then fed every 3-4 days in chemically-defined DNBM, preferably without EGF until a burst of C-RC is observed and the outgrowth of a C-RC population is seen as the dominant, actively expanding population. Once this has occurred, the medium may be supplemented with additional glucose and growth factors, preferably EGF alone, to support rapid C-RC expansion. Explant outgrowths are allowed to expand until the colonies of C-RC are large enough to be harvested for analysis or sub-cultured (1-5×10$^5$ cells) or before colonies begin to touch and their expansion is limited by confluence.

If passaged, the colonies are harvested with trypsin, neutralized with bovine serum albumin or soybean trypsin inhibitor, washed with medium and plated at $1-5\times10^4$ cells per $cm^2$ on collagen-coated plastic and incubated at 37° C. The cultures are fed every 3-4 days with DNBM, to which 10 ng/mL EGF is added the day after plating to assist cell expansion and may contain additional glucose to support rapid growth of C-RC. A cocktail of additional growth factors listed above, known to support regeneration, may be added to support the secondary expansion of certain epithelial C-RC populations as needed. The harvest from this second passage serves as a second substantially pure C-RC population for the tissue sample for comparison and corroboration with harvest of primary C-RC and/or C-RC subsets (such as those observed in ovarian C-RC (FIG. 3)

EXAMPLE 2

Derivation of Populations (C-RC) from Human Ovarian Cancers

Collagen coated plates were prepared by diluting a 5 mg/mL solution of type 1 bovine collagen in sterile tissue culture grade water such that tissue culture plates were coated at 5 µg/$cm^2$. After a 1 hour incubation at room temperature the plates were rinsed with tissue culture grade water and the plating surface was covered with phosphate buffered saline without calcium or magnesium (PBS) until use. Ovarian tumor tissue was delivered by courier at 2-10° C. in a 50 mL centrifuge tube containing RPMI 1640 supplemented with antibiotics and Amphotericin B.

Specimen 1 (from an adult granulosa cell tumor of ovarian origin) was explanted 2 days post-biopsy and specimen 2 (a mucinous cystadenocarcinoma) was explanted 1 day post-biopsy. The tumor tissue (approximately 5-7 $cm^3$) was rinsed three times in sterile PBS supplemented with 10 µg/mL gentamycin at a tissue to volume ratio of at least 1:4. The tissue was then minced into 1-2 $mm^2$ explants and plated onto the aspirated collagen-coated dishes. In addition to the explants obtained following mincing, dissociated cells (ranging in size from 10-30 µM), cell aggregates (ranging in size from 5-200 µM and tissue bits released during mincing of the tissue (ranging in size from >200-about 500 µM) are also obtained.

For both specimens, between 5-8 plates of explants were started in either plating media formulation containing rhEGF, or plating media formulation without rhEGF. In addition, all media formulations contained calcium concentrations <0.1 mM, magnesium concentrations <0.2 mM, and a D-glucose concentration of 2.5 mM at the initiation of cultures.

The plated explants were allowed to air dry for 3-5 minutes at which time any small amount of remaining buffer adjacent to the explants was removed by micropipette and the explant was air-dried for another 3-5 minutes to allow the explants to adhere. When the explants developed a slight haze at the periphery of each piece of tissue, 8-10 mL of DBNM medium, with or without recombinant human epidermal growth factor (rhEGF) supplementation at 10 ng/mL, was added to the explants. All culture plates were incubated in a humidified incubator at 37° C. and at 10% $CO_2$.

At Day 5-6, the majority of explants were removed using sterile forceps especially if the explant had dislodged from the plate or never adhered. For specimen 1 the DNBM media plus cholera toxin included progesterone until Day 8 of culture, after which progesterone was removed from all media preparations. Progesterone was not used in any of the media preparations for specimen 2. Plates were fed every other day with a low glucose, low calcium media with or without rhEGF until Day 8-10, when the glucose concentration was increased to 5 mM using a stock 45% w/v D-glucose solution.

By day 4, some fibroblastic and large epithelial cells with morphology similar to established ovarian cancer cell lines could be seen a short distance from the explants but beyond this, small epithelial cells could be seen extending over the collagen-coated plate, both dispersed as individual cells and as colonies.

The cells exhibited a progression of three morphologies: a proliferating very small epithelial cell (VSEC), bright, rounded but adherent, expanding areas of small dense epithelial cells with a dense nuclei and very little cytoplasm which transitioned to a slightly larger small cuboidal epithelial cell with a translucent nucleus, and more cytoplasm but still with a high nuclear to cytoplasmic ratio. All epithelial cells of this population were significantly smaller than the epithelial or mesenchymal cells close to the explant that exhibited cell line-like morphologies (CLLC) (FIG. 3). Groups of VSEC could sometimes be seen atop the CLLC. VSEC groups and bright clusters were distinct from the occasional large cell mounds generated from CLLC colonies.

The explants were removed at day 6 in Specimen 1 cultures. Culture was continued in base nutrient medium with EGF, without progesterone. Following removal of the explants, the large CLLC epithelial cells showed growth by mounding with little expansion over the dish surface. A second burst of small cells, primarily seen as SDEC, could be seen emerging out from the colonies of CLLC primarily left behind from below and around the explants. Unlike other methods used to derive cancer stem cell lines from ovarian cancer, few if any stromal, endothelial or neural cells survive or proliferate at any time during the course of the primary culture and subsequent passage.

The dissection and mincing of specimen 1 (explanted 2 days post biopsy) produced a slurry of loose cells and small tissue fragments in the mince buffer. The loose material was centrifuged and plated with and without EGF. The loose material produced cultures that favored cell-line like cell (CLLC) plating with early cluster formation, similar to what was seen over later cultures of cell-line like cells following explant removal. In addition fibroblastic cells were seen. For cells cultures regenerated without EGF, a population of CLLC with reduced fibroblast contamination could be observed at day 8 in culture. The colonies looked similar to CLLC colonies (including the generation of large clusters) that remain following explant culture, after the explant is removed. A VSEC population was present by day 8 in culture, however, no burst of SDEC proliferation was observed. Small, rounded very small epithelial cells (VSEC) could be seen at day 10 in culture however, unlike the VSEC from explants, the VSEC from loose cells and aggregates did not generate small dense epithelial cells (SDEC) or SCEC. The cell-line like cells became the dominant cells in these cultures. The use of explant tissue was the preferred method to foster sufficient autocrine and paracrine signaling to support and favor regenerative activation and the initial burst of C-RC proliferation seen in ovarian cancer as a small epithelial cell population consisting of expanding VSEC, SDEC and SCEC.

A second ovarian cancer tissue, Specimen 2 (explanted 1 day post-biopsy), was cultured under the same conditions. Differences were noted in the gross character and consistency of the biopsied tissue. The explants exhibited a limited outgrowth of large, disorganized epithelioid cells that failed to expand further. The morphology of these cells was reminiscent of an ovarian cancer cell line i.e., these cells were cell-line like cells (CLLC). Although overall, the regenerative response from the second tissue was less than the first, a similar small epithelial cell population consisting of VSEC, SDEC and SCEC emerged. The tissue was firmer than specimen 1 and did not yield loose tissue or cells during the preparation of explants. A secondary burst of regeneration was observed in the cultures from this tissue similar to specimen 1. The morphologies and response of the regenerative population was similar between the two specimens but slight morphological differences were discernable beyond the difference in magnitude of response. The VSEC of specimen 2 exhibited a slightly elongated character when adhered to the culture dish while VSEC of specimen 1 remained rounded when adhered. The SCEC of specimen 2 appeared to have a greater effect on the culture substrate. The CLLC grew to a similar extent in both specimens. Specimen 1 showed more organized epithelial character and specimen 2 showing a more disorganized character. In both cases, these CLLC cells were larger than the small epithelial cells (FIG. 3). The size distribution of the small epithelial cells derived from each specimen was comparable (FIG. 3).

The response of ovarian cancer tissue under regenerative stress in vitro as described herein can be distinguished from the experience to date in the derivation of ovarian cancer cell lines or cancer stem cells (Langdon, et al., *Cancer Research*, 48:6166 (1988); Oulette, et al., *BMC Cancer*, 8:152 (2008); Pan, et al., *Methods*, 56:432-9 (2012)); U.S. Pat. No. 8,309,354). The methods described herein result in identification of a subpopulation of cells that have not been identified in the prior art, and at an earlier time frame than is disclosed in the prior art. For example, Pan, et al. describe a method of establishing human ovarian serous carcinoma cell lines in serum-free media, from cancer cells obtained by stripping aggregates of epithelial cancer cells from the tumor tissue and culturing the aggregates in serum-free medium. Pan's method leads to the proliferation of both epithelial and stromal cells, and the eventual selection of an epithelial cell population can take 3-6 months. Consistently, the examples described herein show that when loose cells and aggregates were used as the starting material for cell culture, although VSEC were observed, a burst was not observed and the VSEC did not appear to develop into SCEC and SDEC cells. The CLLC cell was the dominant cell morphology in these cultures, even with little to no proliferation of stromal cells. The method in Pan, et al., represents an advance over methods of deriving cancer cell lines in serum-containing media, however, the outcome is still significantly different from what is observed for ovarian cancer cells cultured using the methods described herein (Example 3), illustrating the unique nature of regenerative activation under the stringent conditions described herein (i.e., forcing the tissues and cells to respond based on endogenous signaling and self-produced factors) compared to the derivation of cancer cell lines using more conventional approaches, most notably where growth supplements are added to promote cell survival and expansion prior to any observed selection of a stem cell or C-RC population rather than after the C-RC have been functionally selected.

Similarly, U.S. Pat. No. 8,309,354 discloses a method of deriving a population of cells containing cancer stem cells, by dissociating solid human tumors and culturing dissociated cells and small cell aggregates in serum-free conditions to obtain cancer stem cell lines that do not senesce upon serial passage, express certain stem cell markers that can vary between cancer types, and exhibit a high efficiency of tumor formation in mice. However the serum-free conditions used to generate these lines are less stringent than those described herein, most notably allowing for the growth and persistence of a stromal cell component, which eventually gives way to a cancer stem cell-like epithelial cell population after an extended period (months) in culture.

The cell behavior seen under the primarily autocrine and paracrine-fueled conditions also unify aspects of both normal and cancer findings regarding cell morphology and stem cell character of ovarian epithelium and ovarian cancer. It supports the notion that the large epithelial and/or mesenchymal-like cells, that lead to the eventual derivation of an ovarian cancer cell line are likely only indirectly related to the regenerative potential of the actual cancer. This notion is supported by the analysis of Gillet et al. (Gillet, et al., *PNAS*, 108:18708 92011)) who found that existing cancer cell lines, including ovarian cancer lines, were more closely related to each other than to the bone fide cancer, and the findings of Strauss et al. (Strauss, et al., *PLOSOne*, 6:e16186 (2011)), that ovarian cancer rapidly lost its epithelial component in culture, leaving a dominant epithelial/mesenchymal phenotype. The methods described herein identify a unique population of regenerative cells, not described by others using serum-containing or serum-free methods, that is readily analyzable. The regenerative population retains a high fidelity to the original tumor, and can therefore be used to gather high fidelity proteomic data that is closely linked to cell behavior.

Activation of the small epithelial cell lineage can be selected for and readily observed as an outgrowth, making identification of subsets (i.e., VSEC, SDEC and SCEC) and delineation of their functional interrelatedness easier to dissect and capture for analysis, without the need for dissociation of tumor explants and separation based on size, or the need for an assumption of stem cell marker expression, which has proven to be ambiguous (Jaggupilli and Elkord *Clinical and Developmental Immunology* (2012), Article ID 708036), Although a very small bright cell population has been described in both cultures of ovarian epithelium from post-menopausal women and in ovarian cancer, the method described herein is unique in its ability to discern this cell lineage in its active form where both common and variable characteristics are more clearly discerned. This offers a means to rapidly identify important cellular relationships and the pivotal phenotypes within the regenerative response of a tumor allowing the capture of high fidelity, regeneration-relevant proteomes and transcriptomes.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An isolated tumor C-RC cell population prepared by
   (a) obtaining a tumor sample from an individual;
   (b) cultivating the tumor sample under conditions that induce a stress response in non-C-RC differentiating and differentiated cells leading to apoptosis and necrosis but permit C-RC cells to propagate through the activation of a regenerative response;

(c) isolating the dominant actively expanding, most rapidly dividing population of cells from step (b); and
(d) culturing the cells to obtain a population of 51% to 100% C-RC,
in a serum-free, defined cell culture medium containing agents selected from the group consisting of agents inducing the apoptosis and/or necrosis of the cells, cAMP elevating agents, agents inhibiting cell-cell adhesion, nitric oxide, tumor necrosis factor-alpha (TNF-α), interleukin 1-beta (IL1-α), interferon-gamma (IFN-γ), agents disrupting cell adhesion, agents interfering with survival of more differentiated cells, and calcium in a concentration of less than about 1 mM calcium,
wherein 80-100% of the C-RC population consists of actively expanding and dividing VSEC, SDEC and SCEC cells and abnormal transit amplifying cells.

* * * * *

UNITED STATES PATENT AND TRADEMARK OFFICE
CERTIFICATE OF CORRECTION

PATENT NO. : 10,247,731 B2  
APPLICATION NO. : 13/774644  
DATED : April 2, 2019  
INVENTOR(S) : Nancy L. Parenteau, Joseph C. Laning and Janet H. Young Page 1 of 2

It is certified that error appears in the above-identified patent and that said Letters Patent is hereby corrected as shown below:

In the Specification

Column 1, Line 37, replace "T cells" with --T cells,--.
Column 2, Line 39, replace "(2010)" with --(2010))--.
Column 3, Line 6, replace "However" with --However,--.
Column 3, Line 14, replace "because" with --because:--.
Column 3, Line 25, replace "Therefore" with --Therefore,--.
Column 3, Line 62, replace "(2011))" with --(2011)--.
Column 3, Line 67, replace "relationships" with --relationships,--.
Column 4, Line 37, replace "serves as an" with --serves as a--.
Column 4, Line 40, replace "Therefore" with --Therefore,--.
Column 4, Line 42, replace "population" with --population,--.
Column 4, Line 59, replace "Therefore" with --Therefore,--.
Column 5, Line 32, replace "successfiffly" with --successfully--.
Column 5, Line 33, replace "However" with --However,--.
Column 5, Line 53, replace "should be" with --should be:--.
Column 5, Line 56, replace "varied" with --varied,--.
Column 5, Line 59, replace "population" with --population,--.
Column 6, Line 26, replace "708036)." with --708036)).--.
Column 6, Line 36, replace "reponse" with --response--.
Column 8, Line 6, replace "pGEX-3X (4A)" with --pGEX-3X--.
Column 8, Line 6, replace "pLent-MULTI (4B)" with --pLent-MULTI--.
Column 11, Line 25, replace "tumor tumor" with --tumor--.
Column 11, Line 55, replace "in" with --In--.
Column 13, Line 67, replace "TCRa" with --TCRα--.
Column 14, Line 3, replace "(2009))" with --(2009)--.
Column 14, Line 8, replace "TCRa" with --TCRα--.
Column 14, Line 9, replace "TCR13" with --TCRβ--.
Column 15, Line 35, replace "T cells" with --T cells.--.
Column 16, Line 13, replace "T cells," with --T cells.--.

Signed and Sealed this  
Thirty-first Day of December, 2019

Andrei Iancu  
*Director of the United States Patent and Trademark Office*

CERTIFICATE OF CORRECTION (continued)
U.S. Pat. No. 10,247,731 B2

Column 17, Line 12, replace "needed" with --needed.--.
Column 17, Line 59, replace "organotoypic" with --organotypic--.
Column 19, Line 11-12, replace "fluorochome" with --fluorochrome--.
Column 20, Line 31, replace "TCRa" with --TCRα--.
Column 20, Line 34, replace "(2009))" with --(2009)--.
Column 21, Line 22, replace ", and" with --and--.
Column 21, Line 54-55, replace "fluorochome" with --fluorochrome--.
Column 23, Line 21, replace "tested" with --tested,--.
Column 25, Line 15, replace "(FIG. 3)" with --(FIG. 3).--.
Column 25, Line 43, replace "are" with --were--.
Column 27, Line 30, replace "(2012))" with --(2012)--.
Column 28, Line 17, replace "18708 92011" with --18708-9 (2011)--.
Column 28, Line 39, replace "708036)," with --708036).--.